(12) United States Patent
Obrstar

(10) Patent No.: US 9,499,857 B2
(45) Date of Patent: Nov. 22, 2016

(54) SELECTION OF TRIPLOID CHO CELLS AND CELL LINES EXPRESSING RECOMBINANT POLYPEPTIDES AS HIGH PRODUCERS

(75) Inventor: Darja Obrstar, Menges (SI)

(73) Assignee: LEK PHARMACEUTICALS D.D., Ljubljana (SI)

( * ) Notice: Subject to any disclaimer, the term of this patent is extended or adjusted under 35 U.S.C. 154(b) by 0 days.

(21) Appl. No.: 13/884,055

(22) PCT Filed: Nov. 9, 2011

(86) PCT No.: PCT/EP2011/069720
§ 371 (c)(1),
(2), (4) Date: Jul. 22, 2013

(87) PCT Pub. No.: WO2012/062794
PCT Pub. Date: May 18, 2012

(65) Prior Publication Data
US 2013/0302816 A1 Nov. 14, 2013

(30) Foreign Application Priority Data

Nov. 10, 2010 (EP) .................................. 10190618

(51) Int. Cl.
C12Q 1/68 (2006.01)
C12N 15/67 (2006.01)
C12P 21/00 (2006.01)

(52) U.S. Cl.
CPC .................. C12Q 1/68 (2013.01); C12N 15/67 (2013.01); C12P 21/00 (2013.01)

(58) Field of Classification Search
None
See application file for complete search history.

(56) References Cited

PUBLICATIONS

Barranco, et al. (1981) "Changes in DNA Distributions and Ploidy of CHO Cells as a Function of Time in Culture", In Vitro, 17(8): 730-34.*
Hasinoff, et al. (2000) "The Catalytic DNA Topoisomerase II Inhibitor Dexrazoxane (ICRF-187) Induces Endopolyploidy in Chinese Hamster Ovary Cells", The Journal of Pharmacology and Experimental Therapeutics, 295(2): 474-83.*
Fu, et al. (1996) "Higher Ploidy in Saccharomyces cerevisiae Supports Enhanced Hepatitis B Virus S Cloned Gene Expression at the Pilot Scale", Biotechnology Progress, 12: 145-48.*
Jarman-Smith (2004) "Characterisation of tetraploid and diploid clones of Spodoptera frugiperda cell line", Cytotechnology, 44: 15-25.*
Vonach, et al. (1998) "Construction of a novel CHO cell line coexpressing human glycosyltransferases and fusion PSGL-1-immunoglobulin G", New Developments and New Applications in Animal Cell Technology, No volume, No number, pp. 181-183.*
Derouazi, et al. (2006) "Genetic characterization of CHO production host DG44 and derivative recombinant cell lines", Biochemical and Biophysical Research Communications, 340(4): 1067-77.*
Jun, et al. (2006) "Limitations to the Development of Humanized Antibody Producing Chinese Hamster Ovary Cells Using Glutamine-Synthetase Gene Amplification", Biotechnology Progress, 22: 770-80.*
Gandor, et al. (1995) "Amplification and expression of recombinant genes in serum-independent Chinese hamster ovary cells", FEBS Letters, 377: 290-94.*
Huang, et al. (2007) "An efficient and targeted gene integration system for high-level antibody expression", Journal of Immunological Methods, 322(1-2): 28-39.*
http://en.wikipedia.org/wiki/Correlation_does_not_imply_causation, "Correlation does not imply causation", Published by Wikipedia, The Wikipedia Foundation, San Francisco, CA, downloaded Feb. 21, 2015.*
Simbulan-Rosenthal, et al. (1999) "Chromosomal abberations in PARP-/- mice: Genome stabilization in immortalized cells by reintroduction of poly(ADP-ribose) polymerase cDNA", Proceedings of National Academy of Science of the United States of America, 96(23): 13191-96.*
Shen, et al. (2005) "Polyploid Formation via Chromosome Duplication Induced by CTP:Phosphocholine Cytidylyltransferase Deficiency and Bcl-2 Overexpression: Identification of Two Novel Endogenous Factors", Journal of Histochemistry & Cytochemistry, 53(6): 725-33.*
Barranco, et al., "Changes in DNA distributions and ploidy of CHO cells as a function of time in culture", In vitro, 17:730-734, 1981.
Jarman-Smith, et al., "Characterisation of tetraploid and diploid clones of Spodoptera frugiperda cell line", Cytotechnology, 44:15-25, 2004.
Lattenmayer, et al., "Characterisation of recombinant CHO cell lines by investigation of protein productivities and genetic parameters", Journal of Biotechnology, 128(4)716-725, 2007.
Lloyd, et al., "Relationship between cell size, cell cycle and specific recombinant protein productivity", Cytotechnology, 34:59-70, 2000.
PCT International Preliminary Report on Patentability issued in International Application No. PCT/EP2011/069720, mailed May 23, 2013.
PCT International Search Report and Written Opinion issued in International Application No. PCT/EP2011/069720, mailed Dec. 20, 2011.
Sandhu, et al., "Prediction of recombinant protein production in an insect cell-baculovirus system using a flow cytometric technique", Journal of Immunological Methods, 325:104-113, 2007.
Suresh, et al., "Biochemical and morphological correlates of growth in diploid and triploid rainbow trout", Journal of Fish Biology, 52(3):588-599, 1998.
Suzuki, et al., "The influence of triploidy on gene expression in the silkworm, Bombyx mori", Heredity, 82:661-667, 1999.
Yamada, et al., "Gene copy number and polyploidy on products formation in yeast", Applied Microbiology and Biotechnology, 88(4):849-857, 2010.

* cited by examiner

Primary Examiner — Robert M Kelly
(74) Attorney, Agent, or Firm — Parker Highlander PLLC

(57) ABSTRACT

The present invention relates to a method for selecting for cells or cell lines that produce a recombinant protein/polypeptide in high yields, the method allowing for the selection of high producer cells or cell lines in an early phase of cell line development, the method comprising the step of determining the nuclear DNA content of the cells or cell lines, wherein the level of the nuclear DNA content of the cells or cell lines positively correlates with the capacity of the cells or cell lines to produce the recombinant protein/polypeptide.

6 Claims, 4 Drawing Sheets

SELECTION OF TRIPLOID CHO CELLS AND CELL LINES EXPRESSING RECOMBINANT POLYPEPTIDES AS HIGH PRODUCERS

This application is a national phase application under 35 U.S.C. §371 of International Application No. PCT/EP2011/069720, filed Nov. 9, 2011, which claims priority to European Application No. 10190618.8, filed Nov. 10, 2010. The entire text of each of the above referenced disclosures is specifically incorporated herein by reference.

The invention relates to the field of recombinant protein production within the broadest meaning. Specifically, the invention relates to a new method of selecting cell clones producing recombinant proteins and polypeptides in high yields. More specifically, the invention relates to a method of determining the nuclear DNA content of cell clones as a tool for the early stage selection of the best-producing cell clone(s). Accordingly, the present invention provides a means to narrow the number of clones with the best-producing potential in early stage of cell line development, thereby reducing both time and costs necessary (i) to select the optimum clone for recombinant protein/polypeptide production and (ii) to produce the recombinant protein/polypeptide.

Before the present invention had been made, various scientists have established a correlation between recombinant protein production and various parameters such as gene copy number and mRNA level. In particular, several scientists observed that the degree of gene amplification is generally proportional to the level of gene expression. Jiang et al. (2006) observed, relative to the parental cell line, a 2- to 3-fold amplification in the gene copy number in recombinant Chinese hamster ovary (CHO) cell lines producing monoclonal antibodies in high yields. However, the mRNA levels in these high producer cell lines were not only 2- to 3-fold but 5- to 7-fold higher than in the respective parental cell line, correlating well with the 5- to 7-fold increase in $q_p$ (specific productivity of the cell line, i.e., the amount of recombinantly produced mAb is 5- to 7-fold increased).

Chusainow et al. (2009) reported contradictory findings regarding gene copy number and level of gene expression when observing recombinant CHO cell lines producing a monoclonal antibody. It was concluded that high gene copy numbers do not always result in high productivity, probably as a result of transcriptional and post-transcriptional limitations in highly amplified sub-clones.

Lattenmayer et al. (2007) compared genetic parameters of recombinant CHO cell lines expressing a fusion protein (EPO-Fc) to their productivity and found a good correlation between the mRNA levels and productivity, whereas high gene copy numbers were not always accompanied by high protein expression.

Another correlation was investigated by another group: The correlation between gene copy number (dose regulation of ploidy series) and transcription level of endogenous genes in an animal system. In detail, Suzuki et al. (1999) studied a dose regulation of ploidy series in the silkworm. The question was whether a cumulative effect or dose compensation occur between ploidy and transcription level in aneuploids. The transcription level of six endogenous genes was analysed by northern blot in diploid and triploid individuals. A very different change of transcription level was detected among the individuals, and only for one individual the endogenous gene dosage effect was shown to be positive.

Another correlation is that between cell size, cell cycle, and recombinant protein production. It was investigated by Lloyd et al. (2000). They observed a relationship between cell size, cell cycle, and recombinant protein production when working with CHO cell lines producing interferon-γ. The results demonstrated that cell size is the major cellular determinant of productivity for all cell lines examined. Product formation was not restricted to any particular cell cycle phase. The specific productivity was lowest when the majority of cells were in G1. It was intermediate when the majority of cells were in S phase, and it was best when the majority of cells were in G2/M. It was hence suggested that cell size is the major cellular determinant of productivity. Conversely, the apparent relationship between cell cycle and productivity is secondary and can simply be ascribed to the increasing size of the cells as they progress through the cell cycle.

An insect cell-baculovirus system was used to explore a putative correlation between the nuclear DNA content and recombinant protein production. Sandhu et al. (2007) observed a correlation between cellular parameters (cell size, granularity, DNA content, measured by flow cytometry) and infection product (enzyme β-galactosidase, briefly β-gal) production. The DNA content was increased by virus multiplication. A correlation between viral DNA synthesis (change in DNA content) and β-gal production was detected only for the early part of the process up to 35 h post infection. For that period, a linear relationship between viral DNA synthesis (number of gene copies) and β-gal production could be demonstrated.

Barranco et al. (1981) were the first to report on triploid cells in a CHO cell line. They describe changes in chromosome number and relative DNA content in cell populations cultured under normal conditions for up to 5 months. They utilised the flow cytometry (microfluorometry, EtBr) technique to measure the DNA content of the cells. The cells were treated with colcemid and dye to allow for the counting and analysis (by microscope) of the chromosomes. As a result they found that the cells remain unchanged regarding both aspects (DNA content and chromosome number) until week 10 of cell culturing. Starting in week 11, an additional cell population appeared in the culture, and that population exhibited a DNA content 1.5 times larger than that of the cells in cultures no more than ten weeks old. Both cell populations were detected in the culture by chromosome counting—one population having 22 chromosomes, the other having 35 chromosomes (1.59 times more). By week 18 of cell culturing, the population exhibiting the increased DNA content predominated. Doubling times, growth fractions, and plating efficiency remain unchanged, however. The authors did not investigate the level of protein expression.

Another, very extensive study of diploid and tetraploid cell lines of *Spodoptera frugiperda* (an insect cell line frequently used for recombinant protein production) was performed by Jarman-Smith et al. (2004). A tetraploid population was found in the parental cell line by flow cytometry and karyotyping, and it was isolated by limited dilution. Tetraploid clones were found to have a cell size about 35% larger than the size of diploid clones. In contrast, the maximum cell density observed in batch cultures of diploid clones was, on average, 185% higher than that of tetraploid clones. Growth rates and metabolic quotients during the exponential phase were similar for both clones. Tetraploid cells infected with wild-type baculovirus and with baculovirus harbouring the green fluorescent protein (GFP) gene resulted in more polyhedra and GFP product, respectively, per cell than did diploid cells. Importantly, the difference between the clones either completely diminished or were reduced to only 50% when the yields (of polyhedra and GFP) were determined per mL of medium. The results indicate that the existing heterogeneity with respect to ploidy level in insect cell populations are correlated to cell growth and product yield. The triploid nuclear DNA content is not mentioned.

To summarize the prior art in regard of protein production by means of recombinant DNA technology and the parameters mentioned above (e.g., gene copy number, mRNA level), it had been shown reiteratively that gene copy number and mRNA level do not (always) correlate with protein production by recombinant DNA technology. No reports exist in the literature focusing on the monitoring of the DNA content in recombinant cell lines. Thus, in an attempt to provide a quick and cost-effective method to select for cell lines producing high amounts of recombinant protein, the inventor of the present invention looked for a correlation between an easily testable property of cell lines and their capacity to produce recombinant proteins (the specific productivity $q_p$ of the cell line). She found such positive correlation between the nuclear DNA content of a cell line and its specific productivity. Accordingly, the inventor developed an easy and quick method allowing for the selection of cells or cell lines producing high amounts of recombinant protein, the method comprising the steps of determining the nuclear DNA content of a cell or cell line and correlating a high content of nuclear DNA with high amounts of recombinant proteins produced by the cell or cell line, that is, establishing a positive correlation between the nuclear DNA content with the amount of the protein produced by the cell/cell line. As the inventor additionally performed a gene copy number analysis (by means of Q-PCR, see Example 8), she was able to eliminate the copy number as a factor influencing the specific productivity of the cells, thereby delimiting her invention from the prior art, e.g., embodied by Jarman-Smith et al. (2004). Virtually any cell or cell line useful as a protein producer in an expression system may be used as the starting cell or cell line for the method developed by the inventor, provided the cell or cell line allows for a stable integration of, or had previously stably integrated the expression plasmid DNA encoding the desired protein. Likewise, the method is by no means limited to any particular type or types of proteins/polypeptides to be expressed. Virtually any protein/polypeptide may be produced in high amounts by recombinant means, be it an antibody light or heavy chain, a toxin, a cytokine, a growth factor, a growth factor receptor, an enzyme, or a hormone.

Accordingly, one aspect of the present invention relates to a method for selecting for cells or cell lines that produce a recombinant protein/polypeptide in high yields (i.e. selecting for cells or cell lines exhibiting good specific productivities) following stable integration of the DNA encoding the recombinant protein/polypeptide into the chromosomal (nuclear) DNA of the cell/cell line, the method allowing for the selection of high producer cells or cell lines in an early phase of cell line development, and the method comprising the step of determining the nuclear DNA content of the cells or cell lines, wherein the level of the nuclear DNA content of the cells or cell lines positively correlates with the capacity of the cells or cell lines to produce the recombinant protein/polypeptide. The inventive method requires only low amounts of cells for analysis, is quick and most cost-effective. The narrowing of the number of clones in an early stage of cell line development on the basis of high nuclear DNA contents (ploidy level) results in the reduction of time and costs. It simultaneously enlarges the pool of high-producing clones and consequently improves the selection of the final clone.

According to a preferred embodiment, the method includes a correlation in that a high level of nuclear DNA content of the cells or cell lines is tantamount to the capacity of the cells or cell lines to produce the recombinant protein or polypeptide in high yields.

According to another preferred embodiment of the inventive method, the cell or cell line producing the recombinant protein or polypeptide in high yields exhibits a specific productivity $q_p$ of not less than 5 pg of the recombinant protein or polypeptide/cell/day, preferably of not less than 6 pg/cell/day, more preferably of not less than 10 pg/cell/day.

According to still another preferred embodiment, the cell or cell line producing the recombinant protein/polypeptide in high yields is a derivative of a CHO cell, such as an SSF3 or CHO K1PD cell.

Another preferred method of the invention is one, wherein the recombinant protein or polypeptide produced in high yields is a light or heavy chain of an antibody, a toxin, an enzyme, a growth factor, a growth factor receptor, or a hormone.

Still another preferred method of the invention is a method, wherein the step of determining the nuclear DNA content is performed by FACS. FACS is performed subsequent to cell lysis, RNA degradation, and addition of propidium iodide as a dye to allow for FACS analysis.

The term "PCL" as used herein means "Parental Cell Line" and relates to a cell line that is the source (origin) of a pool of clones formed by transfection.

The term "pool" as used herein relates to a polyclonal cell population derived from a single transfection of a PCL (as a result of multiple integration events). Each subpopulation within a pool differs from the other subpopulations with respect to the chromosomal location of plasmid DNA integration. Said DNA integration is a stable DNA integration and allows for the stable expression of the gene of interest encoded by the transfected plasmid. As a result, different subpopulations show high heterogeneity in growth characteristic, metabolism, productivity, comparability potential, and stability.

The term "clone" as used herein (unless explained otherwise) relates to an individual homogenous (monoclonal) cell population isolated from a heterogeneous (polyclonal) pool by a cloning procedure. The cloning procedure generates several hundreds to several thousands of homogenous monoclonal cell populations (clones).

The term "stability study experiment" as used herein relates to a study investigating the stability of clones (within the meaning as defined above, that is, homogenous/monoclonal cells). The clones were repeatedly cultivated for 3 to 4 days in 125 ml shake flasks (SF125). Repeatedly cultivating a clone is defined to mean that a suitable growth medium (DM12200A1 in case of CHO K1PD cells or DM12200A5 in case of SSF3 cells) is inoculated with $2\times10^5$ homogenous/monoclonal cells, and the resulting cell cultures are then grown in the incubator at 37° C., 10% $CO_2$, 110 rpm. After 3 to 4 days, a portion of the cells is transferred to fresh DM12200A1 or DM12200A5 medium to reach an initial density of $2\times10^5$ cells/mL. Subsequently, the cells transferred to the fresh medium are grown under the same conditions for 3 to 4 further days, thereby reaching day 7 following the day on which cultivation of the clone was initiated. This procedure is repeated for each selected clone until at least day 63 (at least eight times).

Still within the term "stability study experiment" is the following course of batch-seeding steps. At day 7 following the start of the cultivation of the clone/cells, a portion thereof is seeded as a first batch and cultivated for 10 days i.e., until day 17.

A second batch (i.e., a portion of the cultivated clone/cells at day 14) is seeded at day 14 following the start of cultivating the clone and cultivated for 7 days, i.e., until day 21.

A third batch (i.e., a portion of the cultivated clone/cells at day 21) is seeded at day 21 following the start of cultivating the clone and cultivated for another 7 days, i.e., until day 28.

That procedure is performed for all batches to follow (e.g., the fourth to ninth, or even more).

In order to fully clarify the procedure, it is to be emphasised that the ninth batch (i.e., a portion of the cultivated clone/cells at day 63) is seeded on day 63 following the start of cultivating the clone and cultivated until day 70. That is, cell cultures were repeatedly cultivated for a total period of 10 weeks to obtain nine batches from the entire stability study experiment, as defined herein. In the event twelve batches are desired, the entire stability study experiment will take 13 weeks.

The term "seeding a batch" and the like, as utilised hereinabove, means that the above described and defined repeatedly cultivated 3- to 4-day cultures are inoculated into the appropriate medium (e.g., DM13300A1 in case of K1PD and DM13300A6 in case of SSF3) weekly (at days 7, 14, 21, 28, . . . ) following the start of cultivating the clone to an initial concentration of $4 \times 10^5$ cells/mL. The "batches" are then grown for 10 (only the first batch for each clone) or 7 (for the $2^{nd}$ to $9^{th}$ batch) days in the incubator at 37° C., 10% $CO_2$, 110 rpm. During growth of the 10- or 7-day cultures samples for cell density and titre determination were taken several times. Results were later used to calculate specific cell productivity or to analyze the cells (of a particular) batch for genetic stability.

The term "sample" as used herein relates to a small quantity of cells from, e.g., a cell culture (grown for the experiment performed). A sample may be taken for the purpose of nuclear DNA content measurement (by FACS), cell density or titre determination.

The term "batch" as used herein relates to cultivating cells in a single container (e.g., bottle, flask, or fermenter) a particular period of time (e.g., 7 days, 10 days) under particular growth conditions (e.g., without any feed addition or cell dilution). During cultivation samples were taken from a growing culture for the purpose of cell density or titre determination (to monitor cell growth and recombinant protein production).

The term "specific productivity" ($q_p$) as used herein is defined as the recombinant protein/polypeptide production (given in picograms; pg) per cell per day (pg/cell/day).

The terms "triploid" and "close to triploid" as used herein define the content of nuclear DNA in cells. The nuclear DNA contents "triploid" and "close to triploid" are bigger than a diploid nuclear DNA content and smaller than a tetraploid nuclear DNA content, and triploid or close to triploid cells have a nuclear DNA content that is smaller than that of tetraploid cells but bigger than that of diploid cells.

The term "Hbb intronII" as used herein relates to any nucleic acid molecule exhibiting a sequence of the second intron of the human β-globin (hbb) gene (Hbb intron 2) including 10 bp of the sequence immediately upstream of said Hbb intron 2 in the hbb gene and 10 bp of the sequence immediately downstream of the Hbb intron 2 in the hbb gene. The Hbb intronII exhibits the sequence set out in SEQ ID NO:3.

The term "stable expression" as used herein relates to an expression achieved by integration of the gene of interest into the target cell's chromosome: Initially the gene of interest is introduced into the cell, subsequently into the nucleus, and finally it is integrated into the chromosomal DNA. Stable transfections result in stable cell lines and ensure a long-term, reproducible as well as defined gene expression.

The inventor has observed that the nuclear DNA content distribution among cell clones originating from different pools during cell line development indicated that triploid cell populations are generally better producers of recombinant proteins/polypeptides than diploid populations, regardless of the originating pool and cell line.

Statistical analyses based on the specific productivities ($q_p$) of three different populations (see Example 7, Table 6) showed significant differences between diploid and triploid clones originating from the same pool, whereas no significant difference was observed between diploid clones originating from different pools (obtained following transfection of different PCLs).

The nuclear DNA content of SSF3 and K1PD cells was analysed and compared. SSF3 and K1PD cells are two PCLs derived from the original CHO cell line established by Puck et al. (1958). The analysis showed that one PCL (SSF3) is a mixture of cells with two different nuclear DNA contents (diploid and near-tetraploid), while the other PCL (K1PD) is a homogenous line of diploid cells. Both PCLs were transfected with, e.g., expression constructs coding for the light and heavy chain of GP2017 (a monoclonal antibody directed to tumour necrosis factor, TNF). The pools obtained subsequent to transfection of SSF3 and K1PD cells turned out to be mixtures of cells with different nuclear DNA contents (diploid to tetraploid). The clones derived from the pools (which pools were mixtures of cells with different nuclear DNA contents: diploid to tetraploid) obtained with the homogenous (diploid) PCL (K1PD) were homogenous amongst each other and likewise diploid. This is evidently caused by a significant instability of the tetraploid cells which may not survive the cloning procedure. The majority of clones derived from the non-homogenous PCL (SSF3) were also homogenous amongst each other (close to triploid), while only a few diploid clones were detected.

The initial results were further evaluated during studies investigating the stability of 49 selected clones (best GP2017 producers according to titre). Samples from the clones were collected and analysed: The cell concentration was determined and the titre (amount of protein/polypeptide produced by the cells) measured. These determinations and measurements were performed 2-4 times for each of the nine batches obtained and described above in the stability study experiment. Specific productivities ($q_P$, pg polypeptide/cell/day) were calculated on the basis of these results.

The nuclear DNA content of all 49 best producer clones was analysed twice—first five to six weeks after cloning procedure and second in week 7 of the stability study experiments. A ViCELL® XR analyzer (Beckman Coulter) was used to determine the total and viable cell concentration, while the titres were determined by affinity chromatography. The nuclear DNA content was measured using a FACSCalibur™ flow cytometer (Becton Dickinson). A correlation between nuclear DNA content and specific productivity was observed during the stability study experiment of the 49 selected best-producing clones. The statistical analysis was based on the data obtained with 46 of the 49 clones. It was shown for these clones (producing the light and heavy chain of GP2017, a monoclonal antibody directed to TNF) that triploid cell lines had a significantly higher specific productivity ($P<0.01$) compared to diploid cell lines. Additionally, a comparison of diploid clones from two pools originating from K1PD and SSF3 cells, respectively, was performed and the specific productivities were not significantly different.

In addition, a gene copy number analysis (by means of Q-PCR) was performed for 48 of the above 49 clones (see below, Example 8). A very low correlation ($R^2$ from 0.14 to 0.36) was found between gene copy number and specific productivity. The correlation between the nuclear DNA content and specific productivity was significantly better and demonstrates that the nuclear DNA content can be used in recombinant cell line development (and particularly in recombinant CHO cell line development) as a selection criterion to screen for the best recombinant protein/polypeptide producers.

The present application includes seven figures and six sequences (in the sequence listing) which are explained hereinafter.

Figure 4:
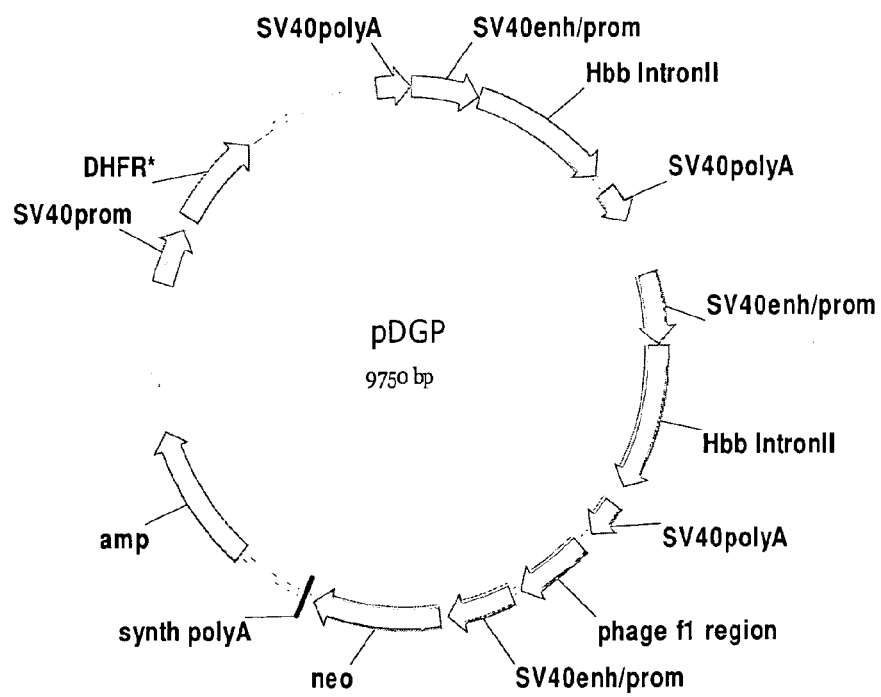

FIG. 4 schematically depicts vector pDGP (9,750 bp) which vector has been used to construct pDGP 2017 by incorporating into pDGP the HC and LC gene of GP2017. The sequence of the vector without the two genes to be expressed (HC and LC of GP2017) is presented in SEQ ID NO:1.

Figure 5:
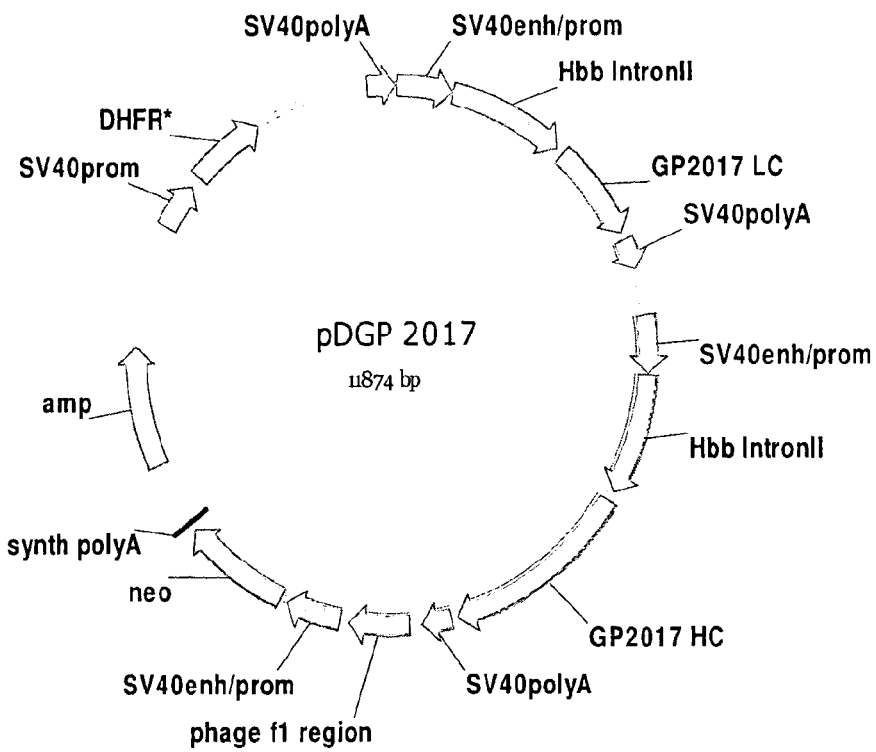

FIG. 5 schematically depicts vector pDGP 2017 (11,874 bp) including the two genes to be expressed (HC, LC genes of GP2017). The sequence of the vector is presented in SEQ ID NO:2. pDGP 2017 was used for the transfection of K1PD cells, as explained in more detail in Example 2.

Figure 6:
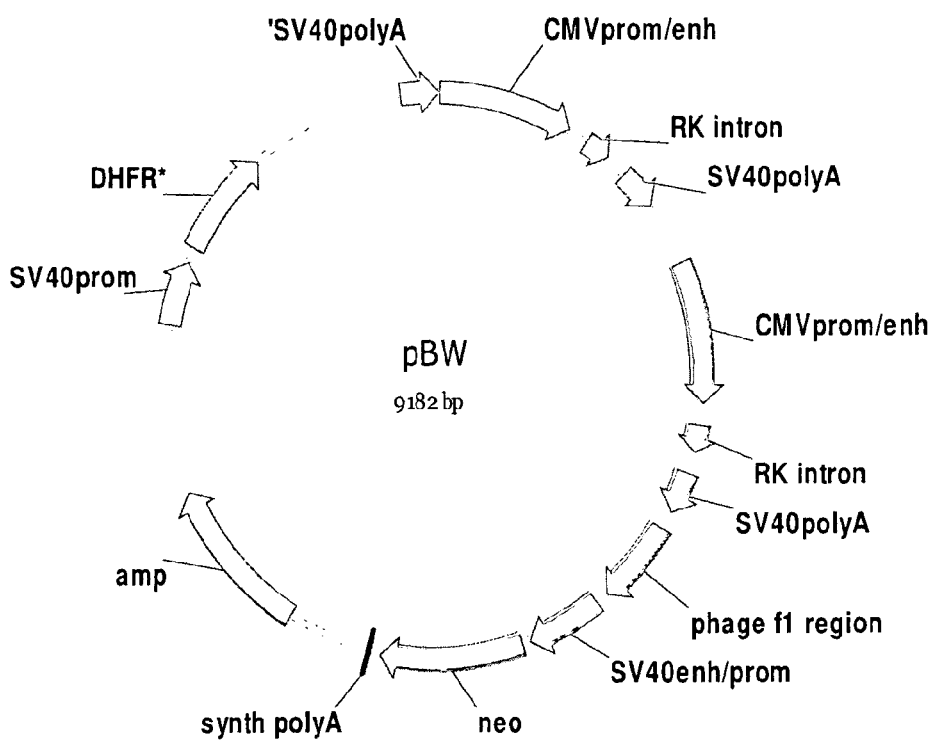

FIG. 6 schematically depicts vector pBW (9,182 bp), which vector has been used to construct pBW GP2017 by incorporating into pBW the HC and LC gene of GP2017. The sequence of the vector is presented in SEQ ID NO:4.

Figure 7:
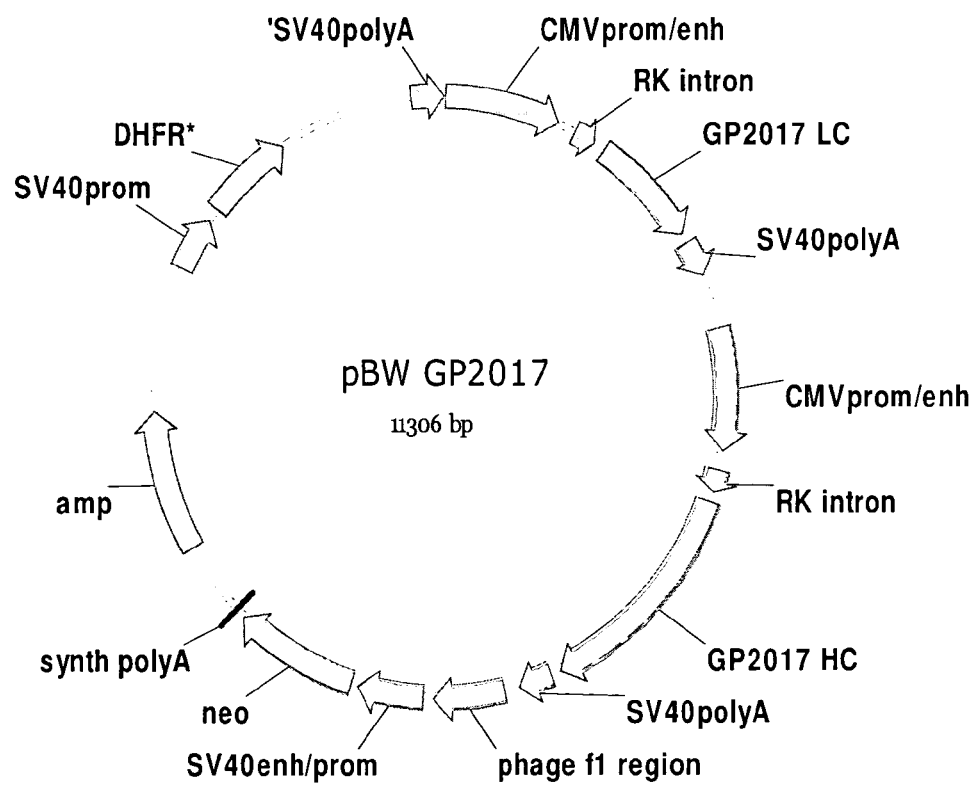

FIG. 7 schematically depicts vector pBW GP2017 (11, 306 bp) including the two genes to be expressed (HC, LC genes of GP2017). The sequence of the vector is presented in SEQ ID NO:5. pBW 2017 was used for the transfection of SSF3 cells, as explained in more detail in Example 2.

SEQ ID NO:1 is the sequence (9,750 bp) of the vector pDGP as depicted in FIG. 4 and used to construct pDGP 2017 (depicted in FIG. 5).

SEQ ID NO:2 is the sequence (11,874 bp) of the vector pDGP 2017 depicted in FIG. 5.

SEQ ID NO:3 is the sequence (870 bp) of the Hbb intronII. The Hbb intronII is comprised twice in each of the vectors depicted in FIGS. 4 and 5.

SEQ ID NO:4 is the sequence (9,182 bp) of the vector pBW used to construct pBW GP2017 depicted in FIG. 6.

SEQ ID NO:5 is the sequence (11,306 bp) of vector pBW GP2017 depicted in FIG. 7.

SEQ ID NO:6 is the sequence (144 bp) of the RK intron. The RK intron is comprised twice in each of the vectors depicted in FIGS. 6 and 7.

The following examples illustrate the present invention in some greater detail. The experiments described in the examples employed various particular standard or in-house media, which may likewise be replaced by other commonly utilised media, because the principal advantage of the invention is not at all dependent upon the (cell culture) medium selected.

EXAMPLE 1

Growth Media

For the purpose of a stability study experiment within the meaning defined above, during the step of repeatedly cultivating the cells, they were grown in media that are routinely used for the cultivation of the respective cells (DM12200A1 for K1PD cells and cells derived therefrom) and in a variant thereof including 1 mg/L insulin and 150 nM MTX (DM12200A5; for SSF3 cells and cells derived therefrom). During the step of seeding a batch, standard production media (DM13300A1 for K1PD cells and derivatives thereof and DM13300A6 including 150 nM MTX for SSF3 cells and derivatives thereof) were employed. All of the above four media (DM12200A1, DM12200A5, DM13300A1, and DM13300A6) are media developed in-house which were customised for use with mammalian cells, in particular CHO-derived cells. The pH of the media regularly ranged from 6.6 to 7.7 (the preferred range was 6.8 to 7.4), the osmolality ranged from 265 to 400 mOsmol/kg (the preferred range was 285 to 380 mOsmol/kg).

EXAMPLE 2

Cell Line Development

The genes coding for each the heavy and light chain of the above-mentioned exemplary antibody GP2017 were inserted into the basic expression vectors—pDGP (FIG. 4) and pBW (FIG. 6), respectively. GP2017 genes insertion resulted in pDGP 2017 (FIG. 5) and pBW GP2017 (FIG. 7), respectively. The heavy and light chain genes were parts of two separate expression cassettes each.

Transfection

The nucleofection method was used to introduce pDGP 2017 or pBW GP2017 linear plasmid DNA into the parental cells (K1PD, SSF3). pDGP 2017 or pBW GP2017 expression constructs were linearised using single cutter restriction endonuclease SwaI.

G418 Selection

Antibiotic selection using geneticin (G418) was the first selection step after transfection. The GP2017-transfected SSF3 or K1PD cells (i.e., all pools obtained) were selected using G418 at a final concentration of 0.8 mg/mL. The antibiotic was added to the cell culture 2-5 days after transfection, when cell viability exceeded 60%. G418 selection usually took 2-4 weeks. After each pool had reached at least 85% cell viability, next selection step was proceeded at a seeding density of $2\times10^5$ viable cells/mL.

MTX Amplification

Different MTX concentrations were tested for the selection of appropriate clones from the pools obtained. The concentration of MTX was adapted to the properties of the cell line employed (SSF3). Two different amplification steps were performed on SSF3 cells using growth medium with 150 nM and 500 nM MTX, respectively. The clones were selected in the medium supplemented with 150 nM MTX.

Figure 1:
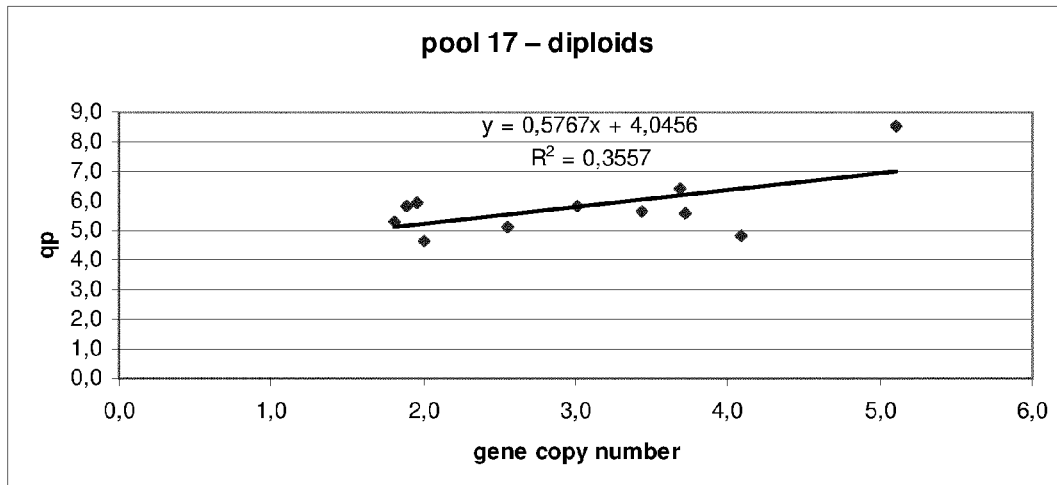
FIG. 1 depicts the extremely poor correlation ($R^2$) between specific productivity ($q_P$, pg polypeptide/cell/day) and gene copy number for diploid clones originating from pool 17, a pool derived from SSF3 cells.
Figure 2:
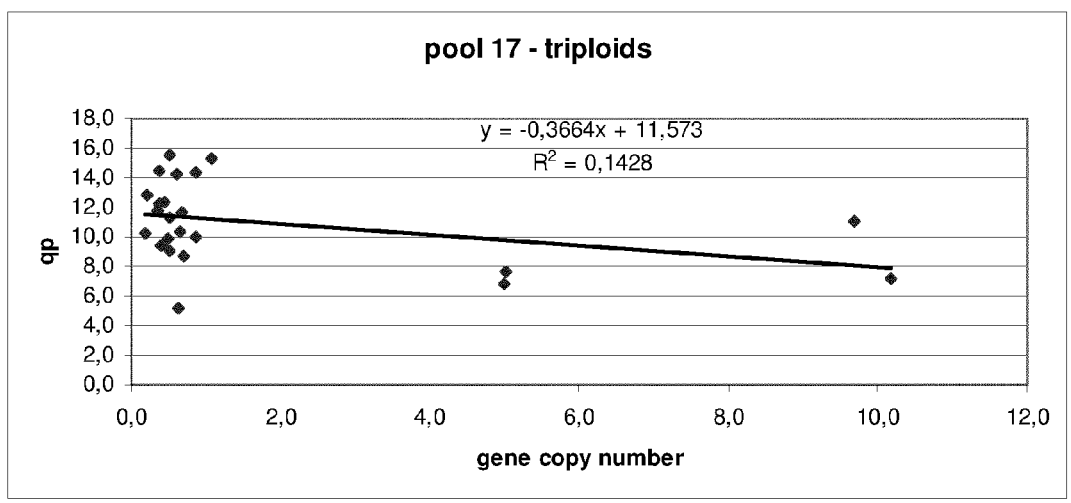
FIG. 2 depicts the comparably poor correlation ($R^2$) between specific productivity ($q_P$, pg polypeptide/cell/day) and gene copy number for triploid clones originating from the same pool (pool 17).
Figure 3:
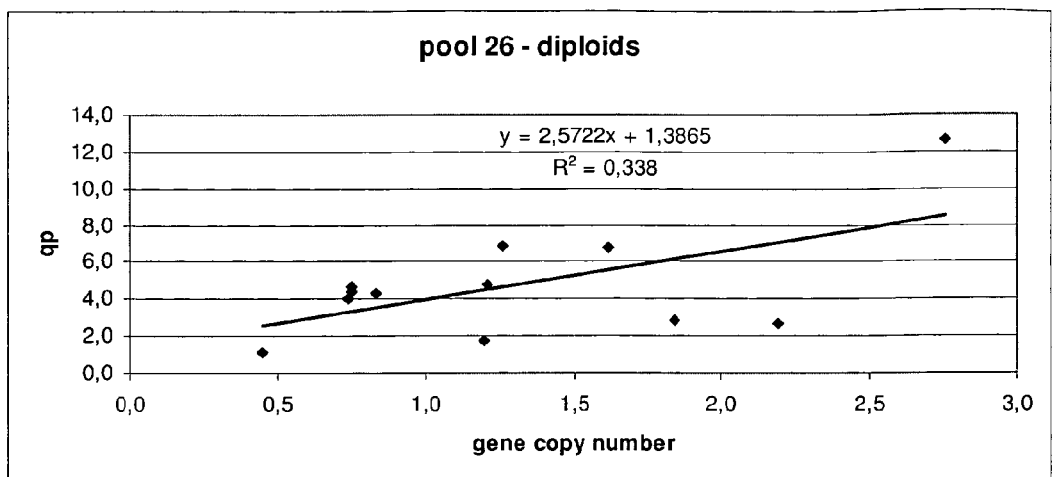
FIG. 3 depicts the likewise extremely poor correlation ($R^2$) between specific productivity ($q_P$, pg polypeptide/cell/day) and gene copy number for diploid clones originating from another pool (pool 26), derived from K1PD cells.

Growth Media Utilised for Growing the Pools/Clones Derived from K1PD and SSF3 Cells/Pools Two pools (pool 17 and pool 26; for the definition of the pools, see the legend to FIGS. 1 to 3 above) were used for selecting clones on the basis of productivity and product quality.

As mentioned earlier in the description, pool 17 originates from the dihydrofolate reductase (DHFR)-deficient SSF3 cell line and its cells contain GP2017 heavy and light chain cDNA inserted in expression vector pBW. The resulting pBW GP2017 vector contains two expression cassettes, each cassette containing one GP2017 cDNA sequence (for the light and heavy chain, respectively), the CMV promoter with RK intron (see SEQ ID NO:6) and the SV40-late-Poly (A)-signal. Additionally, pBW GP2017 contains the genes conferring resistance to neomycin (Neo) and ampicillin (Amp) and a dhfr sequence with the SV40 promoter and SV40-late-Poly(A)-signal. Accordingly, the selection of the clones from pool 17 occurred by addition of G418 and MTX to the medium. The other pool (pool 26) originates from K1PD cells. Its cells likewise contain two expression cassettes. Each of the cassettes contains one GP2017 cDNA sequence (for the light and heavy chain, respectively), the SV 40 promoter with one HbbII intron (see SEQ ID NO:3), and the SV40-late-Poly(A)-signal. The cassettes are inserted into vector pDGP. pDGP 2017, the expression vector including the GP2017 cDNA sequences contains the Neo and Amp resistance genes, the dhfr sequence under the control of the SV40 promoters and the SV40-late-Poly(A)-signal. Selection of the clones from pool 26 occurred by addition of only G418 to the medium.

Approximately 200 clones each from pool 17 and pool 26 were generated and further tested to obtain clones producing high amounts of the antibody heavy and light chains, respectively. After cloning, primary seed lots (PSLs) of all clones were stored (vials, vol: 1 mL; conc: $10^7$ cells/mL) in the gas phase of liquid nitrogen at temperatures below $-130°$ C. 50 of the approximately 2×200 clones were selected according to their titre. 49 thereof were subjected to stability study experiments.

Titres for all clones were measured (see Example 4, subsection 2) and samples for nuclear DNA content measurements by flow cytometry were collected randomly. The nuclear DNA content of 106 clones was analysed. 49/106 clones originated from pool 17, 57/106 clones originated from pool 26 (see Example 4, subsection 4).

EXAMPLE 3

Genetic Stability Studies

Vials of PSLs obtained and stored in Example 2 were thawed in a water bath at 37° C. The content of the vials was transferred into 10 mL of cold medium each and centrifuged 5 min at 80-100×g, 4° C. The supernatants were discarded and the cell sediments gradually diluted into 50 mL medium (pre-heated to 37° C.) to result in cultures of $2 \times 10^5$ viable cells per mL. The 50 mL-cultures were transferred into 250 mL shake-flasks (Corning SF250) and incubated for 3 days in a $CO_2$ shaker-incubator at 37° C., 90 rpm, and 10% $CO_2$. Cells were split every 3-4 days at a density of $2 \times 10^5$ viable cells/mL and added to the appropriate pre-warmed growth medium to maintain exponential growth.

The cultures were further cultivated as described above for the stability study experiment including "repeated cultivation". That is, the cultures were further cultivated in growth medium at a volume of 25 mL in 125 mL shake-flasks (Corning SF125). The growth medium was inoculated with $2 \times 10^5$ viable cells, grown 3 to 4 days in the incubator at 37° C., 10% $CO_2$, 110 rpm. Finally, a part of the culture necessary to reach initial cell density of $2 \times 10^5$ viable cells/mL was transferred to fresh medium. The transferred cells were grown under the same conditions again for 3 to 4 days. This way clones were repeatedly cultivated for 3 to 4 days in 125 mL shake flasks (SF125) for a total period of 10 weeks.

The above described procedure of batch-seeding was performed taking repeatedly cultivated 3- to 4-day cultures at various time points (to obtain the $1^{st}$, $2^{nd}$, $3^{rd}$, ... $9^{th}$, ... $n^{th}$ batch). Samples taken from a seeded batch subsequently grown in the incubator at 37° C., 10% $CO_2$, 110 rpm, as described previously, were later used for cell density and titre determinations. The results were later used to calculate productivity (pg polypeptide/cell/day).

EXAMPLE 4

Sampling and Processing of Samples for Analysis

1. Total and Viable Cell Counting

A ViCELL® XR analyzer (Beckman Coulter) was used to determine the total and viable cell concentrations. The cell concentrations were measured at the end of each passage and 2 to 4 times for each batch during the stability study experiment.

2. Titre Determination

Titres were measured 2 to 4 times for each batch during the stability study experiment. The cells were removed by centrifugation (5 minutes at 80-100×g, 4° C.) and filtrated (MILLEX syringe filter units, Durapore PVDF, pore size 0.2 µm). Fresh samples were analysed (only exceptionally the samples were stored at $-20°$ C. before determination of the titre) by affinity chromatography with protein A.

3. Specific Productivity Determination

The specific productivity $q_p$ was defined as the concentration of the GP2017 product (light or heavy chain of the Ab), as determined in the culture, divided by the integral of viable cell densities (The integral of viable cell densities is the sum of the viable cell density values obtained in the time intervals between the time points when viable cell densities were measured, which time points were distributed between the start (t=0) and the end of each batch (t=7 or 10 days).

4. Nuclear DNA Content Estimation 106 different clones—49 clones from pool 17, 57 clones from pool 26, as mentioned above (Example 2)—were collected randomly five to six weeks after the cloning procedure and analysed subsequently for protein productivity (to identify best producer clones) and nuclear DNA content. Ultimately, the nuclear DNA content of 49 best producer clones from both pools (37 clones from pool 17 and 12 clones from pool 26) was analysed twice—first five to six weeks after cloning procedure and second in week 7 of the stability study experiments.

The cells from suspension cultures were separated from the respective media by centrifugation (23° C., 300×g, 5 min). The cells were washed twice with 4 mL phosphate buffer saline (PBS). $2 \times 10^6$ cells were resuspended in 1 mL 0.1% Triton X-100 in PBS. Subsequently RNase (final concentration: 200 µg/mL) and propidium iodide (PI; final concentration: 10 µg/mL) were added. The cells were incubated 20 min at room temperature in the dark. Before analysis, the cells were filtrated using 50 µm filter to exclude cell clumps. DNA histograms were obtained on a FACSCalibur™ flow cytometer (Becton Dickinson) with a laser tuned to an excitation wavelength of 488 nm (see also: Pozarowski and Darzynkiewicz (1974)). The samples were processed until 10,000 cells were counted in the main G1 channel. At the beginning of each series of measurements, PCLs were measured as a standard. The zero point was not moved during each series of measurements, and the DNA histograms of samples were compared to the DNA histograms of the PCLs and to each other.

EXAMPLE 5

Results of Nuclear DNA Content Measurements for PCLs, Pools 17 and 26, and Clones Originating from Pools 17 and 26

The PCLs were analysed at each series of measurements as a standard. Pools 17 and 26 were analysed multiple times. One PCL (SSF3) was shown to contain a mixed population of cells with a nuclear DNA content of diploid and near-tetraploid level (5 measurements, see Table 1 below). Pool 17 derived from SSF3 contained a mixture of cells with a nuclear DNA content from diploid to tetraploid level (again, 5 measurements, see Table 1 below). In contrast, the other PCL (K1PD) was found to have a homogenous population of diploid cells. However, pool 26 derived from K1PD was shown to contain a mixed population of cells with a nuclear DNA content from diploid to tetraploid level. As speculated in a preceding paragraph herein, the pool consisting of a mixture of cells (diploid to tetraploid) might bring about only diploid clones, because the other (tetraploid) clones simply do not survive the cloning procedure.

As mentioned previously, during development of the recombinant cell lines, approximately 200 clones from each of pools 17 and 26 were generated (i.e., about 400 clones overall). Protein productivity (as determined on the basis of their light/heavy chain titres) was determined for all approximately 400 clones, and about 200 clones (from both pools) were defined as sufficiently well producing clones. From these about 200 clones, 106 were collected randomly (49 clones from pool 17, 57 clones from pool 26) and subsequently analysed again for protein productivity and, additionally, their nuclear DNA content.

Among the collected 49 clones from pool 17, 37 clones were defined as best producer clones (as determined on the basis of their light/heavy chain titres), whereas among the collected 57 clones from pool 26, only 12 clones were defined as best producer clones (as determined on the basis of their light/heavy chain titres).

In parallel, the 49 clones from pool 17 (the above 37 best producer clones and remaining 12 randomly collected clones) and 57 clones from pool 26 (the above 12 best producer clones and remaining 45 randomly collected clones) were analysed for their nuclear DNA content. The overall results are depicted in Tables 1 (for the 49 pool 17 clones) and 2 (for the 57 pool 26 clones) below. The nuclear DNA content among the 49 clones from pool 17 varies from diploid (15), via (close to) triploid (27), to tetraploid (3), with two "clones" exhibiting a mixed cell population ("clones" here is not used in accordance with the definition provided hereinbefore: either two of the cloning procedures were unsuccessful and few different, i.e., polyclonal, cells were collected twice—instead of only one—or the monoclonal cell collected in either case is unstable and changes its nuclear DNA content following cell division(s)), and two other clones that remained undetermined. The nuclear DNA content among the 57 clones from pool 26 was almost invariant: 55 clones were found to exhibit a nuclear DNA content of diploid cells, and only two of the clones exhibit a nuclear DNA content smaller than that of diploid cells. As regards the nuclear DNA content of the 37 best producer clones originating from pool 17, 25 clones had a nuclear DNA content close to triploid level, whereas the 12 best producer clones originating from pool 26 were all diploids (see Tables 1 and 2 below).

One sample of the PCLs (SSF3 and K1PD) as well as of pools 17 and 26 were taken, and the samples were analysed 5 times each, and each measurement entailed the same result. Clones are distributed according to their relative nuclear DNA content. Numbers represent different clones, PCLs or pools.

TABLE 1

| Sample | No. of Analysed Samples | Smaller than Diploid | Size of Diploid | Size Close to Triploid | Size of Tetraploid | Mixed Population | nd |
|---|---|---|---|---|---|---|---|
| PCL SSF3 | 1 | 0 | 0 | 0 | 0 | 1 | 0 |
| Pool 17 | 1 | 0 | 0 | 0 | 0 | 1 | 0 |
| Randomly Collected Clones | 12 | 0 | 5 | 2 | 3 | 0 | 2 |
| Best Producer Clones | 37 | 0 | 10 | 25 | 0 | 2 | 0 | nd = not determined

TABLE 2

| Sample | No. of Analysed Samples | Smaller than Diploid | Size of Diploid | Size Close to Triploid | Size of Tetraploid | Mixed Population |
|---|---|---|---|---|---|---|
| PCL CHO K1PD | 1 | 0 | 1 | 0 | 0 | 0 |
| Pool 26 | 1 | 0 | 0 | 0 | 0 | 1 |
| Randomly Collected Clones | 45 | 2 | 43 | 0 | 0 | 0 |
| Best Producer Clones | 12 | 0 | 12 | 0 | 0 | 0 |

EXAMPLE 6

Results of Correlating the Nuclear DNA Content for the 49 Best Producer Clones with Their Calculated Specific Productivity ($q_p$)

Statistical analysis was based on data collected from the first 10-day batches (beginning) of the stability study experiments. The stability study experiments were started with the 49 best producer clones preliminarily analysed in Example 5. Two of the clones (originating from pool 17, and listed in Table 1 to exhibit mixed populations) were mixtures of cells with two different nuclear DNA contents. These were excluded from the calculations. As to be taken from Tables 1 and 2, the distribution of the clones was as follows: 10 clones with diploid cells and 25 clones with triploid cells (from pool 17); 12 clones with diploid cells (from pool 26). Statistical Analysis of Pool 17 Clones The averaged specific productivities as determined for the clones showed a good correlation with the nuclear DNA content: Clones with a nuclear DNA content close to the triploid level were significantly better producers of exogenous (recombinant) protein than clones having a diploid nuclear DNA content. As to be taken from Table 3, the average $q_p$ of the former clones was about two times higher than the average $q_p$ of the clones having a diploid nuclear DNA content (10.84 pg protein/cell/day vs. 5.35 pg protein/cell/day).

According to statistical analysis, there is a significant difference between diploid and (close to) triploid clone populations originating from pool 17 (t-test: $3.71 \times 10^{-7}$).

Statistical Analysis of Pool 26 Clones

The averaged specific productivities as determined for the clones from pool 26 (all diploids) were 1.2 times higher than the average specific productivity of the clone population with diploid nuclear DNA content from pool 17 (6.53 pg protein/cell/day vs. 5.35 pg protein/cell/day). According to statistical analysis, there is no significant difference between the diploid clone populations originating from pool 17 and the diploid clone populations from pool 26 (t-test: 0.11).

TABLE 3

Statistical Analysis of $q_p$ and Titre Results from the First 10-day Batch of the Genetic Stability Study experiments for Clones from Pool 17

|  | average $q_p$ (pcd) |
|---|---|
| average diploids - pool 17 | 5.35 |
| sd | ±0.73 |
| average triploids - pool 17 | 10.84 |
| sd | ±4.28 |
| t-test (diploids - pool 17/triploids - pool 17) | 3.71E−07 | sd = standard deviation

TABLE 4

Statistical Analysis of $q_p$ Results from the First 10-day Batch of the Genetic Stability Study experiments for Clones from Pool 26

|  | average $q_p$ (pcd) |
|---|---|
| average diploids - pool 26 | 6.53 |
| sd | ±3.27 |
| t-test (diploids - pool 17/diploids - pool 26) | 0.11 |
| t-test (diploids - 26 pool/triploids - pool 17) | 0.00245 | sd = standard deviation

EXAMPLE 7

Results of Correlating the Nuclear DNA Content for the 49 Best Producer Clones with the Calculated Specific Productivity ($q_p$) of Nine Batches Statistical analysis was based on data collected from the $1^{st}$ to $9^{th}$ batch of the stability study experiments. As already mentioned (see Examples 2 and 3), stability study experiments were started with the 49 best producer clones. Stability study experiments for one of them were terminated due to growth problems (a triploid clone from pool 17). Two further clones of the 49 clones were mixtures of cells with two different nuclear DNA contents and were likewise excluded from the calculations (both clones originating from pool 17, see Table 1).

Statistics for consecutive batches 1 to 9 were performed on the remaining 46 clones: 10 diploids and 24 triploids originating from pool 17 and 12 diploids originating from pool 26.

TABLE 5

Statistical Analysis of Specific Productivity Data from Nine Batches of the Genetic Stability Study experiments (Including the First Study Presented in Tables 3 and 4) for Clones Originating from Pools 17 and 26.

| Batch | Pool 17 - Diploids (p17-di) | | | Pool 17 - Triploids (p17-tri) | | | Pool 26 - Diploids (p26-di) | | |
|---|---|---|---|---|---|---|---|---|---|
|  | Average $q_p$ (pcd) | Ratio (p17-di/p17-di) | sd | Average $q_p$ (pcd) | Ratio (p17-tri/p17-di) | sd | Average $q_p$ (pcd) | Ratio (p26-di/p17-di) | sd |
| 1 (10-day) | 5.35 | 1 | 1.92 | 11.06 | 2.07 | 4.31 | 6.53 | 1.22 | 3.26 |
| 2 (7-day)* | 2.25 | 1 | 1.12 | 7.6 | 3.37 | 2.78 | 4.97 | 2.21 | 4.41 |
| 3 (7-day)# | 0 | 0 | 0 | 0 | 0 | 0 | 0 | 0 | 0 |
| 4 (7-day) | 6.96 | 1 | 1.63 | 15.35 | 2.2 | 8.22 | 4.88 | 0.7 | 3.36 |
| 5 (7-day) | 7.79 | 1 | 1.49 | 13.73 | 1.76 | 5.39 | 5.33 | 0.68 | 3.48 |
| 6 (7-day) | 7.02 | 1 | 1.14 | 9.43 | 1.34 | 4.29 | 5.12 | 0.73 | 4.29 |
| 7 (7-day) | 5.98 | 1 | 1.06 | 10.07 | 1.68 | 2.81 | 4.56 | 0.76 | 3.15 |
| 8 (7-day) | 5.68 | 1 | 1.17 | 10.64 | 1.87 | 2.73 | 4.54 | 0.8 | 3.26 |
| 9 (7-day) | 5.85 | 1 | 1.16 | 11.04 | 1.89 | 2.5 | 3.95 | 0.67 | 2.74 |
| Average | 5.86 | 1 | 1.34 | 11.12 | 2.02 | 4.13 | 4.98 | 0.97 | 3.49 |
| Average (w/o batch 2) | 6.09 | 1 | 1.29 | 11.36 | 1.9 | 4.14 | 4.99 | 0.8 | 3.36 |

*Results of batch 2 deviate from results of other batches due to ($7^{th}$ day) cell counting problems.
Statistical analysis was not performed for batch 3 due to incomplete data
sd = standard deviation The figures for the average specific productivities ($q_p$) presented in Table 5 for each batch demonstrate that the ratio between triploids and diploids from pool 17 remains around two (except in batches 2 and 6) during the stability study experiments—similar to what has been described previously (Example 6, Table 3).

The specific productivities of the clones originating from pool 26 are slightly lower than in batch 1 (about 5 vs. 6.53 pg protein/cell/day). The ratios between diploids originating from pool 26 and from pool 17 dropped to below one (except for batch 2).

T-tests of the specific productivities ($q_p$) between diploid and triploid populations originating from pool 17 and diploid populations originating from pools 17 and 26 for each batch were also performed (Table 6).

Statistical results show that the diploid and triploid clone populations (according to $q_p$) remain significantly different (P<0.01) during the stability study experiments (over a period of 10 weeks).

Calculated t-tests of $q_p$ between diploid populations originating from pool 17 and pool 26 vary from batch to batch. Anyhow, both average figures of the t-tests (with and without batch 2) show no significant difference among both diploid populations (P>0.05).

TABLE 6

| Batch | t-test Pool 17-Diploids vs. Pool 17-Triploids | t-test Pool 17-Diploids vs. Pool 26-Diploids |
|---|---|---|
| 1 (10-day) | $3.71 \times 10^{-6}$ | $1.49 \times 10^{-1}$ |
| 2 (7-day) * | $2.35 \times 10^{-9}$ | $3.01 \times 10^{-2}$ |
| 3 (7-day) # | 0 | 0 |
| 4 (7-day) | $3.86 \times 10^{-5}$ | $3.62 \times 10^{-2}$ |
| 5 (7-day) | $1.78 \times 10^{-5}$ | $2.06 \times 10^{-2}$ |
| 6 (7-day) | $9.02 \times 10^{-3}$ | $8.17 \times 10^{-2}$ |
| 7 (7-day) | $4.44 \times 10^{-7}$ | $8.16 \times 10^{-2}$ |
| 8 (7-day) | $1.05 \times 10^{-8}$ | $1.36 \times 10^{-1}$ |
| 9 (7-day) | $9.16 \times 10^{-10}$ | $2.20 \times 10^{-2}$ |
| Average | 0.0011 | 0.0697 |
| Average (w/o Batch 2) | 0.0013 | 0.0747 |

* The results of batch 2 deviate from the results of the other batches due to ($7^{th}$ day) cell counting problems
Statistical analysis was not performed for batch 3 due to incomplete data

EXAMPLE 8

Gene Copy Numbers, Specific Productivities ($q_p$) (Both Results of the $1^{st}$ and $9^{th}$ Batch of the Stability Study Experiments) and Their Correlation Additionally, gene copy number analysis (performed by Q-PCR) was done for 48 of the best producer clones in an attempt to eliminate the gene copy number as a possible factor influencing specific productivity. A very low correlation ($R^2$ from 0.14 to 0.36) was found between the gene copy number and the specific productivity within each group of clones. The results are illustrated in FIGS. 1, 2, and 3.

The light chain gene copy number was determined by Q-PCR at the end of the $1^{st}$ and $9^{th}$ batch of the stability study experiments.

List of References Cited in the Application

Barraco S. C., Shilkun K., Nichols S., Boerwinkle E. G., Adams E. G., Bhuyan B. K. 1981. Changes in DNA distributions and ploidy of CHO cells as a function of time in culture. In vitro 17: 730-734

Chusainow J., Sheng Yang Y., Yeo J. H. M, Toh P. C., Asvadi P, Wong N. S. C., Yap M. G. S. 2009: A Study of Monoclonal Antibody-Producing CHO Cell Lines: What Makes a Stable High Producer?. Biotechnology and Bioengineering 102: 1182-1196

Jarman-Smith R. F., Mannix C., Al-Rubeai M. 2004. Characterisation of tetraploid and diploid clones of Spodoptera frugiperda cell line. Cytotechnology 44. 15-25

Jiang Z., Huang Y., Sharfstein S. T. 2006. Regulation of recombinant monoclonal antibody production in Chinese hamster ovary cells: A comparative study of gene copy number, mRNA level, and protein expression. Biotechnol. Prog. 22: 313-318

Lattenmayer L., Trummer E., Schriebl K., Vorauer-Uhl K., Mueller D., Katinger H., Kunert R. 2007. Characterisation of recombinant CHO cell lines by investigation of protein productivities and genetic parameters. Journal of Biotechnology 128: 716-725

Lloyd D. R., Holmes P., Jackson L. P., Emery A. N., Al-Rubeai. 2000. Relationship between cell size, cell cycle and specific recombinant protein productivity. Cytotechnology 34: 59-70

Pozarowski P. and Darzynkiewicz Z. 1974. Analysis of Cell Cycle by Flow Cytometry. Science 184:1297-1298

Puck T. T., Cieciura S. J., Robinson A. 1958. Genetics of somatic mammalian cells. J. Exp. Med. 108:945-959

Sandhu K. S., Naciri M., Al-Rubeai M. 2007. Prediction of recombinant protein production in an insect cell-baculovirus system using a flow cytometric technique. Journal of Immunological Methods 325: 104-113

Suzuki M. G., Shimada T., Yokoyama T., Kobayashi M. 1999. The influence of triploidy on gene expression in the silkworm, *Bombyx mori*. Heredity 82: 661-667

The invention claimed is:

1. A method of producing a Chinese Hamster Ovary (CHO) cell or a CHO cell line that expresses a recombinant protein/polypeptide in high yields comprising:
   (a) transfecting a CHO cell or CHO cell line with a nucleic acid segment (i) encoding said recombinant protein/polypeptide, and (ii) providing for its expression in the CHO cell or CHO cell line;
   (b) measuring the nuclear DNA content of transfected CHO cells or cell lines; and
   (c) selecting a CHO cell clone or CHO cell line exhibiting a triploid nuclear DNA content,
   wherein the selected CHO cell clone or CHO cell line of step (c) expresses said recombinant protein/polypeptide at high yield.

2. The method of claim 1, wherein the CHO cell clone or CHO cell line is an SSF3 or CHO K1PD cell.

3. The method of claim 1, wherein the recombinant protein or polypeptide expressed in high yields is a light or heavy chain of an antibody, a toxin, an enzyme, a growth factor, a growth factor receptor, or a hormone.

4. The method of claim 1, wherein the measuring the nuclear DNA content occurs by FACS subsequent to cell lysis, RNA degradation, and addition of propidium iodide as a dye.

5. The method of claim 1, wherein the selected CHO cell clone or CHO cell line expressing the recombinant protein/polypeptide in high yields exhibits a specific productivity $q_p$ of not less than 6 pg of the recombinant protein or polypeptide/cell/day.

6. The method of claim 1, wherein the selected CHO cell clone or CHO cell line expressing the recombinant protein/polypeptide in high yields exhibits a specific productivity $q_p$ of not less than 10 pg of recombinant protein or polypeptide/cell/day.

* * * * *

SEQUENCE LISTING

<160> NUMBER OF SEQ ID NOS: 6

<210> SEQ ID NO 1
<211> LENGTH: 9750
<212> TYPE: DNA
<213> ORGANISM: Artificial sequence
<220> FEATURE:
<223> OTHER INFORMATION: Synthetic sequence

<400> SEQUENCE: 1
aattcggatc tgcgcagcac catggcctga aataacctct gaaagaggaa cttggttagg    60
taccttctga ggcggaaaga accagctgtg gaatgtgtgt cagttagggt gtggaaagtc   120

| | |
|---|---|
| cccaggctcc ccagcaggca gaagtatgca aagcatgcat ctcaattagt cagcaaccag | 180 |
| gtgtggaaag tccccaggct ccccagcagg cagaagtatg caaagcatgc atctcaatta | 240 |
| gtcagcaacc atagtcccgc ccctaactcc gcccatcccg ccctaactc cgcccagttc | 300 |
| cgcccattct ccgccccatg gctgactaat ttttttatt tatgcagagg ccgaggccgc | 360 |
| ctcggcctct gagctattcc agaagtagtg aggaggcttt tttggaggcc taggcttttg | 420 |
| caaaaagctt ctcgaggaac ttcagggtga gtctatggga cccttgatgt tttctttccc | 480 |
| cttcttttct atggttaagt tcatgtcata ggaaggggag aagtaacagg gtacagttta | 540 |
| gaatgggaaa cagacgaatg attgcatcag tgtggaagtc tcaggatcgt tttagtttct | 600 |
| tttatttgct gttcataaca attgttttct tttgtttaat tcttgctttc tttttttttc | 660 |
| ttctccgcaa ttttactat tatacttaat gccttaacat tgtgtataac aaaaggaaat | 720 |
| atctctgaga tacattaagt aacttaaaaa aaaactttac acagtctgcc tagtacatta | 780 |
| ctatttggaa tatatgtgtg cttatttgca tattcataat ctccctactt tattttcttt | 840 |
| tattttaat tgatacataa tcattataca tatttatggg ttaaagtgta atgttttaat | 900 |
| atgtgtacac atattgacca aatcagggta attttgcatt tgtaatttta aaaaatgctt | 960 |
| tcttcttta atatactttt ttgttatct tattctaat actttcccta atctctttct | 1020 |
| ttcagggcaa taatgataca atgtatcatg cctctttgca ccattctaaa gaataacagt | 1080 |
| gataatttct gggttaaggc aatagcaata tttctgcata taaatatttc tgcatataaa | 1140 |
| ttgtaactga tgtaagaggt ttcatattgc taatagcagc tacaatccag ctaccattct | 1200 |
| gcttttattt tatggttggg ataaggctgg attattctga gtccaagcta ggcccttttg | 1260 |
| ctaatcatgt tcatacctct tatcttcctc ccacagctcc tgggcagtgt ccactcccag | 1320 |
| gtccaactgc acctcggttc tatcgaaaac gcgtccaccg tcgacccggg cggccgcttc | 1380 |
| cctttagtga gggttaatgc ttcgagcaga catgataaga tacattgatg agtttggaca | 1440 |
| aaccacaact agaatgcagt gaaaaaaatg ctttatttgt gaaatttgtg atgctattgc | 1500 |
| tttatttgta accattataa gctgcaataa acaagttaac aacaacaatt gcattcattt | 1560 |
| tatgtttcag gttcagggggg agatgtggga ggttttttaa gcaagtaaa acctctacaa | 1620 |
| atgtggtaaa atccgataag gatcgatccg ggctggcgta atagcgaaga ggcccgcacc | 1680 |
| gatcgccctt cccaacagtt gcgcagcctg aatggcgaat ggacgcgccc tgtagcggcg | 1740 |
| cattaagcgc ggcgggtgtg gtggttacgc gcagcgtgac cgctacactt gccagcgccc | 1800 |
| tagcgcccgc tcctttcgct ttcttccctt cctttctcgc cacgttcgcc ggctttcccc | 1860 |
| gtcaagctct aaatcggggg ctcccttag ggttccgatt tagagcttta cggcacctcg | 1920 |
| accgcaaaaa acttgatttg ggtgatggtt cacgatctgc gcagcaccat ggcctgaaat | 1980 |
| aacctctgaa agaggaactt ggttaggtac cttctgaggc ggaaagaacc agctgtggaa | 2040 |
| tgtgtgtcag ttagggtgtg gaaagtcccc aggctcccca gcaggcagaa gtatgcaaag | 2100 |
| catgcatctc aattagtcag caaccaggtg tggaaagtcc ccaggctccc cagcaggcag | 2160 |
| aagtatgcaa agcatgcatc tcaattagtc agcaaccata gtcccgcccc taactccgcc | 2220 |
| catcccgccc ctaactccgc ccagttccgc ccattctccg ccccatggct gactaatttt | 2280 |
| ttttatttat gcagaggccg aggccgcctc ggcctctgag ctattccaga agtagtgagg | 2340 |
| aggcttttt ggaggcctag gcttttgcaa aaagcttctc gaggaacttc agggtgagtc | 2400 |
| tatgggaccc ttgatgtttt ctttcccctt cttttctatg gttaagttca tgtcatagga | 2460 |
| aggggagaag taacagggta cagtttagaa tgggaaacag acgaatgatt gcatcagtgt | 2520 |

```
ggaagtctca ggatcgtttt agtttctttt atttgctgtt cataacaatt gttttctttt    2580
gtttaattct tgctttcttt ttttttcttc tccgcaattt ttactattat acttaatgcc    2640
ttaacattgt gtataacaaa aggaaatatc tctgagatac attaagtaac ttaaaaaaaa    2700 actttcacaca gtctgcctag tacattacta tttggaatat atgtgtgctt atttgcatat   2760
tcataatctc cctactttat tttcttttat ttttaattga tacataatca ttatacatat    2820
ttatgggtta aagtgtaatg ttttaatatg tgtacacata ttgaccaaat cagggtaatt    2880
ttgcatttgt aattttaaaa aatgctttct tcttttaata tacttttttg tttatcttat    2940
ttctaatact ttccctaatc tctttcttttc agggcaataa tgatacaatg tatcatgcct   3000
ctttgcacca ttctaaagaa taacagtgat aatttctggg ttaaggcaat agcaatattt    3060
ctgcatataa atatttctgc atataaattg taactgatgt aagaggtttc atattgctaa    3120
tagcagctac aatccagcta ccattctgct tttatttat ggttgggata aggctggatt     3180
attctgagtc caagctaggc cttttgcta atcatgttca tacctcttat cttcctccca     3240
cagctcctgg gcagtgtcca ctcccaggtc caactgcacc tcggttctat cgaaaggcgc    3300
gtactagtca tatgccaccg gcgcgccggg cggccgcttc cctttagtga gggttaatgc    3360
ttcgagcaga catgataaga tacattgatg agtttggaca aaccacaact agaatgcagt    3420
gaaaaaaatg ctttatttgt gaaatttgtg atgctattgc tttatttgta accattataa    3480
gctgcaataa acaagttaac aacaacaatt gcattcattt tatgtttcag gttcagggggg  3540 agatgtggga ggtttttttaa agcaagtaaa acctctacaa atgtggtaaa atccgataag   3600
gatcgatccg ggctggcgta atagcgaaga ggcccgcacc gatcgccctt cccaacagtt    3660
gcgcagcctg aatggcgaat ggacgcgccc tgtagcggcg cattaagcgc ggcgggtgtg    3720
gtggttacgc gcagcgtgac cgctacactt gccagcgccc tagcgcccgc tcctttcgct    3780
ttcttccctt cctttctcgc cacgttcgcc ggctttcccc gtcaagctct aaatcggggg    3840
ctccctttag ggttccgatt tagagcttta cggcacctcg accgcaaaaa acttgatttg    3900
ggtgatggtt cacgtagtgg gccatcgccc tgatagacgg ttttttcgccc tttgacgttg   3960 gagtccacgt tctttaatag tggactcttg ttccaaactg gaacaacact caaccctatc    4020
tcggtctatt cttttgattt ataagggatt ttgccgattt cggcctattg gttaaaaaat    4080
gagctgattt aacaaatatt taacgcgaat tttaacaaaa tattaacgtt tacaatttcg    4140
cctgatgcgg tattttctcc ttacgcatct gtgcggtatt tcacaccgca tacgcggatc    4200
tgcgcagcac catggcctga aataacctct gaaagaggaa cttggttagg taccttctga    4260
ggcggaaaga accagctgtg gaatgtgtgt cagttagggt gtggaaagtc cccaggctcc    4320
ccagcaggca gaagtatgca aagcatgcat ctcaattagt cagcaaccag gtgtggaaag    4380
tccccaggct ccccagcagg cagaagtatg caaagcatgc atctcaatta gtcagcaacc    4440
atagtcccgc ccctaactcc gcccatcccg ccctaactc cgcccagttc cgcccattct     4500
ccgccccatg gctgactaat ttttttttatt tatgcagagg ccgaggccgc ctcggcctct   4560
gagctattcc agaagtagtg aggaggcttt tttggaggcc taggcttttg caaaaagctt    4620
gattcttctg acacaacagt ctcgaactta aggctagagc caccatgatt gaacaagatg    4680
gattgcacgc aggttctccg gccgcttggg tggagaggct attcggctat gactgggcac    4740
aacagacaat cggctgctct gatgccgccg tgttccggct gtcagcgcag gggcgcccgg    4800 ttcttttttgt caagaccgac ctgtccggtg ccctgaatga actgcaggac gaggcagcgc   4860
ggctatcgtg gctggccacg acgggcgttc cttgcgcagc tgtgctcgac gttgtcactg    4920
```

```
aagcgggaag ggactggctg ctattgggcg aagtgccggg gcaggatctc ctgtcatctc    4980
accttgctcc tgccgagaaa gtatccatca tggctgatgc aatgcggcgg ctgcatacgc    5040
ttgatccggc tacctgccca ttcgaccacc aagcgaaaca tcgcatcgag cgagcacgta    5100
ctcggatgga agccggtctt gtcgatcagg atgatctgga cgaagagcat caggggctcg    5160
cgccagccga actgttcgcc aggctcaagg cgcgcatgcc cgacggcgag gatctcgtcg    5220
tgacccatgg cgatgcctgc ttgccgaata tcatggtgaa aaatggccgc ttttctggat    5280
tcatcgactg tggccggctg ggtgtggcgg accgctatca ggacatagcg ttggctaccc    5340
gtgatattgc tgaagagctt ggcggcgaat gggctgaccg cttcctcgtg ctttacggta    5400
tcgccgctcc cgattcgcag cgcatcgcct tctatcgcct tcttgacgag ttcttctgag    5460
cgggactctg gggttcgaaa tgaccgacca agcgacgccc aacctgccat cacgatggcc    5520
gcaataaaat atctttattt tcattacatc tgtgtgttgg ttttttgtgt gaatcgatag    5580
cgataaggat ccgcgtatgg tgcactctca gtacaatctg ctctgatgcc gcatagttaa    5640
gccagccccg acaccgcca  acacccgctg acgcgccctg acgggcttgt ctgctcccgg    5700
catccgctta cagacaagct gtgaccgtct ccgggagctg catgtgtcag aggttttcac    5760
cgtcatcacc gaaacgcgcg agacgaaagg gcctcgtgat acgcctattt ttataggtta    5820
atgtcatgat aataatggtt tcttagacgt caggtggcac ttttcgggga atgtgcgcg     5880 gaacccctat ttgtttattt ttctaaatac attcaaatat gtatccgctc atgagacaat    5940
aaccctgata aatgcttcaa taatattgaa aaaggaagag tatgagtatt caacatttcc    6000
gtgtcgccct tattccctt  tttgcggcat tttgccttcc tgttttgct  cacccagaaa    6060 cgctggtgaa agtaaaagat gctgaagatc agttgggtgc acgagtgggt tacatcgaac    6120
tggatctcaa cagcggtaag atccttgaga gttttcgccc cgaagaacgt tttccaatga    6180
tgagcacttt taaagttctg ctatgtggcg cggtattatc ccgtattgac gccgggcaag    6240
agcaactcgg tcgccgcata cactattctc agaatgactt ggttgagtac tcaccagtca    6300
cagaaaagca tcttacggat ggcatgacag taagagaatt atgcagtgct gccataacca    6360
tgagtgataa cactgcggcc aacttacttc tgacaacgat cggaggaccg aaggagctaa    6420 ccgcttttt  gcacaacatg ggggatcatg taactcgcct tgatcgttgg gaaccggagc    6480
tgaatgaagc cataccaaac gacgagcgtg acaccacgat gcctgtagca atggcaacaa    6540
cgttgcgcaa actattaact ggcgaactac ttactctagc ttcccggcaa caattaatag    6600
actggatgga ggcggataaa gttgcaggac cacttctgcg ctcggccctt ccggctggct    6660
ggtttattgc tgataaatct ggagccggtg agcgtgggtc tcgcggtatc attgcagcac    6720
tggggccaga tggtaagccc tcccgtatcg tagttatcta cacgacgggg agtcaggcaa    6780
ctatggatga acgaaataga cagatcgctg agataggtgc ctcactgatt aagcattggt    6840
aactgtcaga ccaagtttac tcatatatac tttagattga tttaaaactt catttttaat    6900
ttaaaaggat ctaggtgaag atcctttttg ataatctcat gaccaaaatc ccttaacgtg    6960
agttttcgtt ccactgagcg tcagaccccg tagaaaagat caaaggatct tcttgagatc    7020
ctttttttct gcgcgtaatc tgctgcttgc aaacaaaaaa accaccgcta ccagcggtgg    7080
tttgtttgcc ggatcaagag ctaccaactc tttttccgaa ggtaactggc ttcagcagag    7140
cgcagatacc aaatactgtc cttctagtgt agccgtagtt aggccaccac ttcaagaact    7200
ctgtagcacc gcctacatac ctcgctctgc taatcctgtt accagtggct gctgccagtg    7260
```

```
gcgataagtc gtgtcttacc gggttggact caagacgata gttaccggat aaggcgcagc    7320
ggtcgggctg aacgggggt tcgtgcacac agcccagctt ggagcgaacg acctacaccg     7380
aactgagata cctacagcgt gagctatgag aaagcgccac gcttcccgaa gggagaaagg    7440
cggacaggta tccggtaagc ggcagggtcg aacaggaga gcgcacgagg gagcttccag     7500
ggggaaacgc ctggtatctt tatagtcctg tcgggtttcg ccacctctga cttgagcgtc    7560 gattttgtg atgctcgtca gggggcgga gcctatggaa aaacgccagc aacgcggcct      7620
ttttacggtt cctggccttt tgctggcctt ttgctcacat ggctcgacag atccatttaa    7680
attttcaccg tcatcaccga aacgcgcgag gcagctgtgg aatgtgtgtc agttagggtg    7740
tggaaagtcc ccaggctccc cagcaggcag aagtatgcaa agcatgcatc tcaattagtc    7800
agcaaccagg tgtggaaagt ccccaggctc cccagcaggc agaagtatgc aaagcatgca    7860
tctcaattag tcagcaacca tagtcccgcc cctaactccg cccatcccgc ccctaactcc    7920
gcccagttcc gcccattctc cgccccatgg ctgactaatt tttttattt atgcagaggc     7980 cgaggccgcc tcggccctct gagctattcc agaagtagtg aggaggcttt tttggaggcc    8040
taggcttttg caaaaagcta attcgagctc ggtaccccca aacttgacgg caatcctagc    8100
gtgaaggctg taggattttt atccccgctg ccatcatggt tcgaccattg aactgcatcg    8160
tcgccgtgtc ccaaaatatg gggattggca agaacggaga ccgacccctgg cctccgctca   8220 ggaacgagtt caagtacttc caagaatga ccacaacctc ttcagtggaa ggtaaacaga     8280
atctggtgat tatgggtagg aaaacctggt ctccattcc tgagaagaat cgacctttaa     8340
aggacagaat taatatagtt ctcagtagag aactcaaaga accaccacga ggagctcatt    8400
ttcttgccaa aagtttggat gatgccttaa gacttattga acaaccggaa ttggcaagta    8460
aagtagacat ggtttggata gtcggaggca gttctgttta ccaggaagcc atgaatcaac    8520
caggccacct cagactcttt gtgacaagga tcatgcagga atttgaaagt gacacgtttt    8580
tcccagaaat tgatttgggg aaatataaac ttctcccaga atacccaggc gtcctctctg    8640
aggtccagga ggaaaaaggc atcaagtata agtttgaagt ctacgagaag aaagactaac    8700
aggaagatgc tttcaagttc tctgctcccc tcctaaagct atgcattttt ataagaccat    8760
gggggatgct cgatcccctc gcgagttggt tcagctgctg cctgaggctg acgacctcg     8820 cggagttcta ccggcagtgc aaatccgtcg gcatccagga aaccagcagc ggctatccgc    8880
gcatccatgc ccccgaactg caggagtggg gaggcacgat ggccgctttg gtccggatct    8940
ttgtgaagga accttacttc tgtggtgtga cataattgga caaactacct acagagattt    9000
aaagctctaa ggtaaatata aaattttaa gtgtataatg tgttaaacta ctgattctaa     9060
ttgtttgtgt attttagatt ccaacctatg gaactgatga atgggagcag tggtggaatg    9120
cctttaatga ggaaaacctg ttttgctcag aagaaatgcc atctagtgat gatgaggcta    9180
ctgctgactc tcaacattct actcctccaa aaagaagag aaaggtagaa gaccccaagg     9240
actttccttc agaattgcta agtttttga gtcatgctgt gtttagtaat agaactcttg     9300
cttgctttgc tatttacacc acaaaggaaa aagctgcact gctatacaag aaaattatgg    9360
aaaaatattc tgtaaccttt ataagtaggc ataacagtta taatcataac atactgtttt    9420
ttcttactcc acacaggcat agagtgtctg ctattaataa ctatgctcaa aaattgtgta   9480
cctttagctt tttaatttgt aaaggggtta ataaggaata tttgatgtat agtgccttga    9540
ctagagatca taatcagcca taccacattt gtagaggttt tacttgcttt aaaaaacctc    9600
ccacacctcc ccctgaacct gaaacataaa atgaatgcaa ttgttgttgt taacttgttt    9660
```

```
attgcagctt ataatggtta caaataaagc aatagcatca caaatttcac aaataaagca      9720
tttttttcac tgcattctag ttgtggtttg                                      9750

<210> SEQ ID NO 2
<211> LENGTH: 11874
<212> TYPE: DNA
<213> ORGANISM: Artificial Sequence
<220> FEATURE:
<223> OTHER INFORMATION: Synthetic Sequence

<400> SEQUENCE: 2
aattcggatc tgcgcagcac catggcctga ataacctct gaaagaggaa cttggttagg        60
taccttctga ggcggaaaga accagctgtg aatgtgtgt cagttagggt gtggaaagtc       120
cccaggctcc ccagcaggca gaagtatgca aagcatgcat ctcaattagt cagcaaccag      180
gtgtggaaag tccccaggct ccccagcagg cagaagtatg caaagcatgc atctcaatta      240
gtcagcaacc atagtcccgc ccctaactcc gcccatcccg ccctaactc cgcccagttc       300 cgcccattct ccgccccatg ctgactaat ttttttatt tatgcagagg ccgaggccgc        360
ctcggcctct gagctattcc agaagtagtg aggaggcttt tttggaggcc taggcttttg      420
caaaaagctt ctcgaggaac ttcagggtga gtctatggga cccttgatgt tttctttccc      480
cttcttttct atggttaagt tcatgtcata ggaaggggag aagtaacagg gtacagttta     540
gaatgggaaa cagacgaatg attgcatcag tgtggaagtc tcaggatcgt tttagtttct      600
tttatttgct gttcataaca attgttttct tttgtttaat tcttgctttc ttttttttc      660 ttctccgcaa ttttttactat tatacttaat gccttaacat tgtgtataac aaaaggaaat    720
atctctgaga tacattaagt aacttaaaaa aaaactttac acagtctgcc tagtacatta      780
ctatttggaa tatatgtgtg cttatttgca tattcataat ctccctactt tattttcttt     840
tatttttaat tgatacataa tcattataca tatttatggg ttaaagtgta atgttttaat     900
atgtgtacac atattgacca aatcagggta attttgcatt tgtaattta aaaaatgctt      960 tcttcttta atatactttt tgtttatct tatttctaat actttcccta atctctttct     1020
ttcagggcaa taatgataca atgtatcatg cctctttgca ccattctaaa gaataacagt    1080
gataatttct gggttaaggc aatagcaata tttctgcata taaatatttc tgcatataaa    1140
ttgtaactga tgtaagaggt ttcatattgc taatagcagc tacaatccag ctaccattct    1200
gcttttattt tatggttggg ataaggctgg attattctga gtccaagcta ggcccttttg    1260
ctaatcatgt tcatacctct tatcttcctc ccacagctcc tgggcagtgt ccactcccag    1320
gtccaactgc acctcggttc tatcgaaaac gcgtccacca tgtccgtgct gacccaggtg    1380
ctggccctgc tgctgctgtg gctgaccggc accagatgcg acatccagat gacccagtcc    1440
ccctcctccc tgtccgcctc cgtgggcgac agagtgacca tcacctgccg ggcctcccag    1500
ggcatccgga actacctggc ctggtatcag cagaagcctg gcaaggcccc taagctgctg    1560
atctacgccg cctccaccct gcagtccggc gtgccttccc ggttctccgg ctccggcagc    1620
ggcaccgact tcaccctgac catctcctcc ctgcagcctg aggacgtggc cacctactac    1680
tgccagcggt acaacagagc cccttacacc ttcggccagg gcaccaaggt ggagatcaag    1740
cgtacggtgg ccgctccttc cgtgttcatc ttccctccct ccgacgagca gctgaagtcc    1800
ggcaccgcca gcgtcgtctg cctgctgaac aacttctacc ctcggagggc caaggtgcag    1860
tggaaggtgg acaacgccct gcagagcggc aactcccagg aatccgtcac cgagcaggac    1920
```

```
tccaaggaca gcacctactc cctgtccagc accctgaccc tgtccaaggc cgactacgag    1980
aagcacaagg tgtacgcctg cgaggtcacc caccagggcc tgtcctcccc cgtgaccaag    2040
tccttcaacc ggggcgagtg ctgatgagtc gacccgggcg gccgcttccc tttagtgagg    2100
gttaatgctt cgagcagaca tgataagata cattgatgag tttggacaaa ccacaactag    2160
aatgcagtga aaaaaatgct ttatttgtga aatttgtgat gctattgctt tatttgtaac    2220
cattataagc tgcaataaac aagttaacaa caacaattgc attcatttta tgtttcaggt    2280 tcaggggag atgtgggagg ttttttaaag caagtaaaac ctctacaaat gtggtaaaat    2340
ccgataagga tcgatccggg ctggcgtaat agcgaagagg cccgcaccga tcgcccttcc    2400
caacagttgc gcagcctgaa tggcgaatgg acgcgccctg tagcggcgca ttaagcgcgg    2460
cgggtgtggt ggttacgcgc agcgtgaccg ctacacttgc cagcgcccta gcgcccgctc    2520
ctttcgcttt cttcccttcc tttctcgcca cgttcgccgg ctttccccgt caagctctaa    2580
atcgggggct ccctttaggg ttccgattta gagcttacg gcacctcgac cgcaaaaaac    2640
ttgatttggg tgatggttca cgatctgcgc agcaccatgg cctgaaataa cctctgaaag    2700
aggaacttgg ttaggtacct tctgaggcgg aaagaaccag ctgtggaatg tgtgtcagtt    2760
agggtgtgga aagtccccag gctccccagc aggcagaagt atgcaaagca tgcatctcaa    2820
ttagtcagca accaggtgtg gaaagtcccc aggctcccca gcaggcagaa gtatgcaaag    2880
catgcatctc aattagtcag caaccatagt cccgccccta actccgccca tcccgcccct    2940
aactccgccc agttccgccc attctccgcc ccatggctga ctaattttt ttatttatgc    3000 agaggccgag gccgcctcgg cctctgagct attccagaag tagtgaggag gcttttttgg    3060
aggcctaggc ttttgcaaaa agcttctcga ggaacttcag ggtgagtcta tgggacccct    3120
gatgttttct ttccccttct tttctatggt taagttcatg tcataggaag gggagaagta    3180
acagggtaca gtttagaatg ggaaacagac gaatgattgc atcagtgtgg aagtctcagg    3240
atcgttttag tttctttat ttgctgttca taacaattgt tttcttttgt ttaattcttg    3300
cttttctttt ttttcttctc cgcaattttt actattatac ttaatgcctt aacattgtgt    3360
ataacaaaag gaaatatctc tgagatacat taagtaactt aaaaaaaaac tttacacagt    3420
ctgcctagta cattactatt tggaatatat gtgtgcttat ttgcatattc ataatctccc    3480
tactttattt tcttttattt ttaattgata cataatcatt atacatattt atgggttaaa    3540
gtgtaatgtt ttaatatgtg tacacatatt gaccaaatca gggtaatttt gcatttgtaa    3600
ttttaaaaaa tgctttcttc ttttaatata cttttttgtt tatcttattt ctaatacttt    3660
ccctaatctc tttctttcag ggcaataatg atacaatgta tcatgcctct ttgcaccatt    3720
ctaaagaata acagtgataa tttctgggtt aaggcaatag caatatttct gcatataaat    3780
atttctgcat ataaattgta actgatgtaa gaggtttcat attgctaata gcagctacaa    3840
tccagctacc attctgcttt tattttatgg ttgggataag gctggattat tctgagtcca    3900
agctaggccc ttttgctaat catgttcata cctcttatct tcctcccaca gctcctgggc    3960
agtgtccact cccaggtcca actgcacctc ggttctatcg aaaggcgcgt actagtcata    4020
tgccaccatg gcctgggtct ggaccctgcc tttcctgatg gccgctgccc agtccgtgca    4080
ggccgaggtg cagctggtcg agtctggcgg cggactggtg cagcctggcc ggtccctgcg    4140
gctgtcctgc gccgcctccg gcttcacctt cgacgactac gccatgcact gggtccgcca    4200
ggcccctggc aaaggcctcg agtgggtgtc cgccatcacc tggaactccg gccacatcga    4260
ctacgccgac tccgtggagg gccggttcac catctcccgg gacaacgcca agaactccct    4320
```

```
gtacctgcag atgaactccc tgcgggccga ggacaccgcc gtgtactact gcgccaaggt    4380
gtcctacctg tccaccgcct cctccctgga ctactgggc  cagggcaccc tggtcaccgt    4440
gtcctccgcc tccaccaagg gccctccgt  gttccctctg gccccttcct ccaagtccac    4500
ctccggcggc accgccgctc tgggctgcct ggtcaaggac tacttccctg agcctgtgac    4560
agtgtcctgg aactctggcg ccctgaccag cggcgtgcac accttccctg ccgtgctgca    4620
gtcctccggc ctgtactccc tgtcctccgt cgtcacagtg ccttcctcca gcctgggcac    4680
ccagacctac atctgcaacg tgaaccacaa gccttccaac accaaggtgg acaagaaggt    4740
ggagcctaag tcctgcgaca gaccccacac ctgccctccc tgccctgccc ctgagctgct    4800
gggcggacct tccgtgttcc tgttccctcc taagcctaag gacaccctga tgatctcccg    4860
gacccctgag gtcacctgcg tggtggtgga cgtgtcccac gaggatcctg aggtcaagtt    4920
caattggtac gtggacggcg tggaggtgca caacgctaag accaagcctc gggaagagca    4980
gtacaactcc acctaccggg tggtgtccgt gctgaccgtg ctgcaccagg actggctgaa    5040
cggcaaagaa tacaagtgca aggtctccaa caaggccctg cctgccccca tcgagaaaac    5100
catctccaag gccaagggcc agcctcgcga gcctcaggtg tacaccctgc ctccctcccg    5160
ggacgagctg accaagaacc aggtgtccct gacctgtctg gtcaagggct tctacccttc    5220
cgatatcgcc gtggagtggg agtccaacgg ccagcctgag aacaactaca agaccacccc    5280
tcctgtgctg gactccgacg gctccttctt cctgtactcc aagctgaccg tggacaagtc    5340
ccggtggcag cagggcaacg tgttctcctg ctccgtgatg cacgaggccc tgcacaacca    5400
ctacacccag aagtccctgt ccctgagccc tggcaagtga tgaggcgcgc cgggcggccg    5460
cttcccttta gtgagggtta atgcttcgag cagacatgat aagatacatt gatgagtttg    5520
gacaaaccac aactagaatg cagtgaaaaa aatgctttat ttgtgaaatt tgtgatgcta    5580
ttgctttatt tgtaaccatt ataagctgca ataaacaagt taacaacaac aattgcattc    5640
attttatgtt tcaggttcag ggggagatgt gggaggtttt ttaaagcaag taaaacctct    5700
acaaatgtgg taaaatccga taaggatcga tccgggctgg cgtaatagcg aagaggcccg    5760
caccgatcgc ccttcccaac agttgcgcag cctgaatggc gaatggacgc gccctgtagc    5820
ggcgcattaa gcgcggcggg tgtggtggtt acgcgcagcg tgaccgctac acttgccagc    5880
gccctagcgc ccgctccttt cgctttcttc ccttcctttc tcgccacgtt cgccggcttt    5940
ccccgtcaag ctctaaatcg ggggctccct ttagggttcc gatttagagc tttacggcac    6000
ctcgaccgca aaaaacttga tttgggtgat ggttcacgta gtgggccatc gccctgatag    6060 acggttttc  gccctttgac gttggagtcc acgttcttta atagtggact cttgttccaa    6120
actggaacaa cactcaaccc tatctcggtc tattcttttg atttataagg gattttgccg    6180
atttcggcct attggttaaa aaatgagctg atttaacaaa tatttaacgc gaattttaac    6240
aaaatattaa cgtttacaat ttcgcctgat gcggtatttt ctccttacgc atctgtgcgg    6300
tatttcacac cgcatacgcg gatctgcgca gcaccatggc ctgaaataac ctctgaaaga    6360
ggaacttggt taggtacctt ctgaggcgga agaaccagc  tgtggaatgt gtgtcagtta    6420
gggtgtggaa agtccccagg ctccccagca ggcagaagta tgcaaagcat gcatctcaat    6480
tagtcagcaa ccaggtgtgg aaagtcccca ggctccccag caggcagaag tatgcaaagc    6540
atgcatctca attagtcagc aaccatagtc ccgcccctaa ctccgcccat cccgccccta    6600
actccgccca gttccgccca ttctccgccc catggctgac taatttttttt tatttatgca    6660
```

```
gaggccgagg ccgcctcggc ctctgagcta ttccagaagt agtgaggagg ctttttttgga    6720 ggcctaggct tttgcaaaaa gcttgattct tctgacacaa cagtctcgaa cttaaggcta    6780
gagccaccat gattgaacaa gatggattgc acgcaggttc tccggccgct tgggtggaga    6840
ggctattcgg ctatgactgg gcacaacaga caatcggctg ctctgatgcc gccgtgttcc    6900
ggctgtcagc gcaggggcgc ccggttcttt ttgtcaagac cgacctgtcc ggtgccctga    6960
atgaactgca ggacgaggca gcgcggctat cgtggctggc cacgacgggc gttccttgcg    7020
cagctgtgct cgacgttgtc actgaagcgg gaagggactg gctgctattg ggcgaagtgc    7080
cggggcagga tctcctgtca tctcaccttg ctcctgccga aaagtatccc atcatggctg    7140
atgcaatgcg gcggctgcat acgcttgatc cggctacctg cccattcgac caccaagcga    7200
aacatcgcat cgagcgagca cgtactcgga tggaagccgg tcttgtcgat caggatgatc    7260
tggacgaaga gcatcagggg ctcgcgccag ccgaactgtt cgccaggctc aaggcgcgca    7320
tgcccgacgg cgaggatctc gtcgtgaccc atggcgatgc ctgcttgccg aatatcatgg    7380
tggaaaatgg ccgcttttct ggattcatcg actgtggccg ctgggtgtg gcggaccgct    7440 atcaggacat agcgttggct acccgtgata ttgctgaaga gcttggcggc gaatgggctg    7500
accgcttcct cgtgctttac ggtatcgccg ctcccgattc gcagcgcatc gccttctatc    7560
gccttcttga cgagttcttc tgagcgggac tctggggttc gaaatgaccg accaagcgac    7620
gcccaacctg ccatcacgat ggccgcaata aaatatcttt attttcatta catctgtgtg    7680
ttggtttttt gtgtgaatcg atagcgataa ggatccgcgt atggtgcact ctcagtacaa    7740
tctgctctga tgccgcatag ttaagccagc cccgacaccc gccaacaccc gctgacgcgc    7800
cctgacgggc ttgtctgctc ccggcatccg cttacagaca agctgtgacc gtctccggga    7860
gctgcatgtg tcagaggttt tcaccgtcat caccgaaacg cgcgagacga aagggcctcg    7920
tgatacgcct atttttatag gttaatgtca tgataataat ggtttcttag acgtcaggtg    7980
gcacttttcg gggaaatgtg cgcggaaccc ctatttgttt attttttctaa atacattcaa    8040 atatgtatcc gctcatgaga caataaccct gataaatgct tcaataatat tgaaaaagga    8100
agagtatgag tattcaacat ttccgtgtcg cccttattcc cttttttgcg cattttgcc    8160 ttcctgtttt tgctcaccca gaaacgctgg tgaaagtaaa agatgctgaa gatcagttgg    8220
gtgcacgagt gggttacatc gaactggatc tcaacagcgg taagatcctt gagagttttc    8280
gccccgaaga acgttttcca atgatgagca cttttaaagt tctgctatgt ggcgcggtat    8340
tatcccgtat tgacgccggg caagagcaac tcggtcgccg catacactat tctcagaatg    8400
acttggttga gtactcacca gtcacagaaa agcatcttac ggatggcatg acagtaagag    8460
aattatgcag tgctgccata accatgagtg ataacactgc ggccaactta cttctgacaa    8520
cgatcggagg accgaaggag ctaaccgctt ttttgcacaa catgggggat catgtaactc    8580
gccttgatcg ttgggaaccg gagctgaatg aagccatacc aaacgacgag cgtgacacca    8640
cgatgcctgt agcaatggca acaacgttgc gcaaactatt aactggcgaa ctacttactc    8700
tagcttcccg gcaacaatta atagactgga tggaggcgga taaagttgca ggaccacttc    8760
tgcgctcggc ccttccggct ggctggttta ttgctgataa atctggagcc ggtgagcgtg    8820
ggtctcgcgg tatcattgca gcactggggc cagatggtaa gccctcccgt atcgtagtta    8880
tctacacgac ggggagtcag gcaactatgg atgaacgaaa tagacagatc gctgagatag    8940
gtgcctcact gattaagcat tggtaactgt cagaccaagt ttactcatat atactttaga    9000
ttgatttaaa acttcatttt taatttaaaa ggatctaggt gaagatcctt tttgataatc    9060
```

```
tcatgaccaa aatcccttaa cgtgagtttt cgttccactg agcgtcgac  cccgtagaaa   9120 agatcaaagg atcttcttga gatcctttt  ttctgcgcgt aatctgctgc ttgcaaacaa   9180
aaaaaccacc gctaccagcg gtggtttgtt tgccggatca agagctacca actcttttc   9240 cgaaggtaac tggcttcagc agagcgcaga taccaaatac tgtccttcta gtgtagccgt   9300
agttaggcca ccacttcaag aactctgtag caccgcctac atacctcgct ctgctaatcc   9360
tgttaccagt ggctgctgcc agtggcgata agtcgtgtct taccgggttg gactcaagac   9420
gatagttacc ggataaggcg cagcggtcgg gctgaacggg gggttcgtgc acacagccca   9480
gcttggagcg aacgacctac accgaactga gatacctaca gcgtgagcta tgagaaagcg   9540
ccacgcttcc cgaagggaga aaggcggaca ggtatccggt aagcggcagg gtcggaacag   9600
gagagcgcac gagggagctt ccaggggaa  acgcctggta tctttatagt cctgtcgggt   9660
ttcgccacct ctgacttgag cgtcgatttt tgtgatgctc gtcagggggg cggagcctat   9720
ggaaaaacgc cagcaacgcg gcctttttac ggttcctggc cttttgctgg cctttgctc    9780 acatggctcg acagatccat ttaaattttc accgtcatca ccgaaacgcg cgaggcagct   9840
gtggaatgtg tgtcagttag ggtgtggaaa gtccccaggc tccccagcag gcagaagtat   9900
gcaaagcatg catctcaatt agtcagcaac caggtgtgga aagtccccag gctccccagc   9960
aggcagaagt atgcaaagca tgcatctcaa ttagtcagca accatagtcc cgcccctaac   10020
tccgcccatc ccgcccctaa ctccgcccag ttccgcccat tctccgcccc atggctgact   10080 aattttttt  attatgcag  aggccgaggc cgcctcggcc ctctgagcta ttccagaagt   10140
agtgaggagg ctttttggga ggcctaggct tttgcaaaaa gctaattcga gctcggtacc   10200
cccaaacttg acggcaatcc tagcgtgaag gctggtagga ttttatcccc gctgccatca   10260
tggttcgacc attgaactgc atcgtcgccg tgtcccaaaa tatggggatt ggcaagaacg   10320
gagaccgacc ctggcctccg ctcaggaacg agttcaagta cttccaaaga atgaccacaa   10380
cctcttcagt ggaaggtaaa cagaatctgg tgattatggg taggaaaacc tggttctcca   10440
ttcctgagaa gaatcgacct ttaaaggaca gaattaatat agttctcagt agagaactca   10500
aagaaccacc acgaggagct cattttcttg ccaaaagttt ggatgatgcc ttaagactta   10560
ttgaacaacc ggaattggca agtaaagtag acatggtttg gatagtcgga ggcagttctg   10620
tttaccagga agccatgaat caaccaggcc acctcagact ctttgtgaca aggatcatgc   10680
aggaatttga aagtgacacg ttttccccag aaattgattt ggggaaatat aaacttctcc   10740
cagaataccc aggcgtcctc tctgaggtcc aggaggaaaa aggcatcaag tataagtttg   10800
aagtctacga gaagaaagac taacaggaag atgctttcaa gttctctgct cccctcctaa   10860
agctatgcat ttttataaga ccatggggga tgctcgatcc cctcgcgagt tggttcagct   10920
gctgcctgag gctggacgac ctcgcggagt tctaccggca gtgcaaatcc gtcggcatcc   10980
aggaaaccag cagcggctat ccgcgcatcc atgcccccga actgcaggag tggggaggca   11040
cgatggccgc tttggtccgg atctttgtga aggaacctta cttctgtggt gtgacataat   11100
tggacaaact acctcagag  atttaaagct ctaaggtaaa tataaaattt ttaagtgtat   11160
aatgtgttaa actactgatt ctaattgttt gtgtatttta gattccaacc tatgaactg    11220 atgaatggga gcagtggtgg aatgccttta atgaggaaaa cctgttttgc tcagaagaaa   11280
tgccatctag tgatgatgag gctactgctg actctcaaca ttctactcct ccaaaaaaga   11340
agagaaaggt agaagacccc aaggactttc cttcagaatt gctaagtttt ttgagtcatg   11400
```

| | |
|---|---:|
| ctgtgtttag taatagaact cttgcttgct ttgctattta caccacaaag gaaaaagctg | 11460 |
| cactgctata caagaaaatt atggaaaaat attctgtaac ctttataagt aggcataaca | 11520 |
| gttataatca taacatactg ttttttctta ctccacacag gcatagagtg tctgctatta | 11580 |
| ataactatgc tcaaaaattg tgtaccctta gctttttaat ttgtaaaggg gttaataagg | 11640 |
| aatatttgat gtatagtgcc ttgactagag atcataatca gccataccac atttgtagag | 11700 |
| gttttacttg ctttaaaaaa cctcccacac ctcccccctga acctgaaaca taaaatgaat | 11760 |
| gcaattgttg ttgttaactt gtttattgca gcttataatg gttacaaata aagcaatagc | 11820 |
| atcacaaatt tcacaaataa agcatttttt tcactgcatt ctagttgtgg tttg | 11874 |

<210> SEQ ID NO 3
<211> LENGTH: 870
<212> TYPE: DNA
<213> ORGANISM: Artificial Sequence
<220> FEATURE:
<223> OTHER INFORMATION: Synthetic Sequence

<400> SEQUENCE: 3

| | |
|---|---:|
| gaacttcagg gtgagtctat gggacccttg atgttttctt tccccttctt ttctatggtt | 60 |
| aagttcatgt cataggaagg ggagaagtaa cagggtacga tttagaatgg gaaacagacg | 120 |
| aatgattgca tcagtgtgga agtctcagga tcgttttagt ttcttttatt tgctgttcat | 180 |
| aacaattgtt ttcttttgtt taattcttgc ttttcttttt tttcttctcc gcaattttta | 240 |
| ctattatact taatgcctta acattgtgta taacaaaagg aaatatctct gagatacatt | 300 |
| aagtaactta aaaaaaaact ttacacagtc tgcctagtac attactattt ggaatatatg | 360 |
| tgtgcttatt tgcatattca taatctccct actttatttt cttttatttt taattgatac | 420 |
| ataatcatta tacatattta tggggttaaag tgtaatgttt taatatgtgt acacatattg | 480 |
| accaaatcag ggtaattttg catttgtaat tttaaaaaat gctttcttct tttaatatac | 540 |
| ttttttgttt atcttatttc taatactttc cctaatctct ttctttcagg gcaataatga | 600 |
| tacaatgtat catgcctctt tgcaccattc taaagaataa cagtgataat ttctgggtta | 660 |
| aggcaatagc aatatttctg catataaata tttctgcata taaattgtaa ctgatgtaag | 720 |
| aggtttcata ttgctaatag cagctacaat ccagctacca ttctgctttt attttatggt | 780 |
| tgggataagg ctggattatt ctgagtccaa gctaggccct tttgctaatc atgttcatac | 840 |
| ctcttatctt cctcccacag ctcctgggca | 870 |

<210> SEQ ID NO 4
<211> LENGTH: 9182
<212> TYPE: DNA
<213> ORGANISM: Artificial Sequence
<220> FEATURE:
<223> OTHER INFORMATION: Synthetic Sequence

<400> SEQUENCE: 4

| | |
|---|---:|
| aattcggatc ttcaatattg gccattagcc atattattca ttggttatat agcataaatc | 60 |
| aatattggct attggccatt gcatacgttg tatctatatc ataatatgta catttatatt | 120 |
| ggctcatgtc caatatgacc gccatgttgg cattgattat tgactagtta ttaatagtaa | 180 |
| tcaattacgg ggtcattagt tcatagccca tatatggagt tccgcgttac ataacttacg | 240 |
| gtaaatggcc cgcctggctg accgcccaac gacccccgcc cattgacgtc aataatgacg | 300 |
| tatgttccca tagtaacgcc aatagggact ttccattgac gtcaatgggt ggagtattta | 360 |
| cggtaaactg cccacttggc agtacatcaa gtgtatcata tgccaagtac gccccctatt | 420 |

```
gacgtcaatg acggtaaatg gcccgcctgg cattatgccc agtacatgac cttatgggac    480
tttcctactt ggcagtacat ctacgtatta gtcatcgcta ttaccatggt gatgcggttt    540
tggcagtaca tcaatgggcg tggatagcgg tttgactcac ggggatttcc aagtctccac    600
cccattgacg tcaatgggag tttgttttgg caccaaaatc aacgggactt tccaaaatgt    660
cgtaacaact ccgccccatt gacgcaaatg ggcggtaggc gtgtacggtg gaggtctat    720
ataagcagag ctcgtttagt gaaccgtcag atcgcctgga cgccatcc acgctgtttt    780
gacctccata aagacaccg gaccgatcc agcctccgcg ccgggaacg gtgcattgga    840
acgcggattc cccgtgccaa gagtgacgta agtaccgcct atagagtcta taggcccacc    900
cccttggctt cgttagaacg cggctacaat aatacataa cctta tgtat catacacata    960
cgatttaggt gacactatag aataacatcc actttgcctt tctctccaca ggtgtccact    1020
cccaggtcca actgcacctc ggttctatcg aaaacgcgcc tctagacctg caggccacca    1080
gatctgtcga cccgggcggc cgcttcc ctt tagtgagggt taatgcttcg agcagacatg    1140
ataagataca ttgatgagtt tggacaaacc acaactgaa tgcagtgaaa aaatgctttt    1200
atttgtgaaa tttgtgatgc tattgcttta tttgtaacca ttataagctg caataaacaa    1260
gttaacaaca acaattgcat tcattttatg tttcaggttc agggggagat gtgggaggtt    1320
ttttaaagca agtaaaacct ctacaaatgt ggtaaaatcc gataaggatc gatccgggct    1380
ggcgtaatag cgaagaggcc cgcaccgatc gcccttccca acagttgcgc agcctgaatg    1440
gcgaatggac gcgccctgta gcggcgcatt aagcgcggcg ggtgtggtgg ttacgcgcag    1500
cgtgaccgct acacttgcca gcgccctagc gcccgctcct ttcgctttct tcccttcctt    1560
tctcgccacg ttcgccggct ttccccgtca gctctaaat cggggctcc ctttagggtt    1620
ccgatttaga gctttacggc acctcgaccg caaaaaactt gatttgggtg atggttcacg    1680
atcttcaata ttggccatta gccatattat tcattggtta tatagcataa atcaatattg    1740
gctattggcc attgcatacg ttgtatctat atcataatat gtacatttat attggctcat    1800
gtccaatatg accgccatgt tggcattgat tattgactag ttattaatag taatcaatta    1860
cggggtcatt agttcatagc ccatatatgg agttccgcgt tacataactt acggtaaatg    1920
gcccgcctgg ctgaccgccc aacgacccc gcccattgac gtcaataatg acgtatgttc    1980
ccatagtaac gccaataggg actttccatt gacgtcaatg ggtggagtat ttacggtaaa    2040
ctgcccactt ggcagtacat caagtgtatc atatgccaag tacgccccct attgacgtca    2100
atgacggtaa atggcccgcc tggcattatg cccagtacat gaccttatgg actttcc ta    2160
cttggcagta catctacgta ttagtcatcg ctattaccat ggtgatgcgg ttttggcagt    2220
acatcaatgg gcgtggatag cggtttgact cacggggatt ccaagtctc accccattg    2280
acgtcaatgg gagtttgttt tggcaccaaa atcaacggga ctttccaaaa tgtcgtaaca    2340
actccgcccc attgacgcaa atgggcggta ggcgtgtacg gtgggaggtc tatataagca    2400
gagctcgttt agtgaaccgt cagatcgcct ggagacgcca tccacgctgt tttgacctcc    2460
atagaagaca ccgggaccga tccagcctcc gcggccggga acggtgcatt ggaacgcgga    2520
ttccccgtgc caagagtgac gtaagtaccg cctatagagt ctataggccc accccccttgg    2580
cttcgttaga acgcggctac aattaataca taaccttatg tatcatacac atacgattta    2640
ggtgacacta tagaataaca tccactttgc ctttctctcc acaggtgtcc actcccaggt    2700
ccaactgcac ctcggttcta tcgaaaacgc gtccaccggc gcgccctag agtcgacccg    2760
```

```
ggcggccgct tcccttagt gagggttaat gcttcgagca gacatgataa gatacattga   2820
tgagtttgga caaaccacaa ctagaatgca gtgaaaaaaa tgctttattt gtgaaatttg   2880
tgatgctatt gctttatttg taaccattat aagctgcaat aaacaagtta caacaacaa    2940 ttgcattcat tttatgtttc aggttcaggg ggagatgtgg gaggttttt  aaagcaagta   3000 aaacctctac aaatgtggta aaatccgata aggatcgatc cgggctggcg taatagcgaa   3060
gaggcccgca ccgatcgccc ttcccaacag ttgcgcagcc tgaatggcga atggacgcgc   3120
cctgtagcgg cgcattaagc gcggcgggtg tggtggttac gcgcagcgtg accgctacac   3180
ttgccagcgc cctagcgccc gctcctttcg ctttcttccc ttcctttctc gccacgttcg   3240
ccggctttcc ccgtcaagct ctaaatcggg ggctcccttt agggttccga tttagagctt   3300
tacggcacct cgaccgcaaa aaacttgatt tgggtgatgg ttcacgtagt gggccatcgc   3360
cctgatagac ggtttttcgc cctttgacgt tggagtccac gttctttaat agtggactct   3420
tgttccaaac tggaacaaca ctcaacccta tctcggtcta ttcttttgat ttataaggga   3480
ttttgccgat ttcggcctat tggttaaaaa atgagctgat ttaacaaata tttaacgcga   3540
attttaacaa aatattaacg tttacaattt cgcctgatgc ggtattttct ccttacgcat   3600
ctgtgcggta tttcacaccg catacgcgga tctgcgcagc accatggcct gaaataacct   3660
ctgaaagagg aacttggtta ggtaccttct gaggcggaaa gaaccagctg tggaatgtgt   3720
gtcagttagg gtgtggaaag tccccaggct ccccagcagg cagaagtatg caaagcatgc   3780
atctcaatta gtcagcaacc aggtgtggaa agtccccagg ctccccagca ggcagaagta   3840
tgcaaagcat gcatctcaat tagtcagcaa ccatagtccc gcccctaact ccgcccatcc   3900
cgcccctaac tccgcccagt tccgcccatt ctccgcccca tggctgacta attttttta    3960 tttatgcaga ggccgaggcc gcctcggcct ctgagctatt ccagaagtag tgaggaggct   4020
tttttggagg cctaggcttt tgcaaaaagc ttgattcttc tgacacaaca gtctcgaact   4080
taaggctaga gccaccatga ttgaacaaga tggattgcac gcaggttctc cggccgcttg   4140
ggtggagagg ctattcggct atgactgggc acaacagaca atcggctgct ctgatgccgc   4200
cgtgttccgg ctgtcagcgc aggggcgccc ggttcttttt gtcaagaccg acctgtccgg   4260
tgccctgaat gaactgcagg acgaggcagc gcggctatcg tggctggcca cgacgggcgt   4320
tccttgcgca gctgtgctcg acgttgtcac tgaagcggga agggactggc tgctattggg   4380
cgaagtgccg gggcaggatc tcctgtcatc tcaccttgct cctgccgaga agtatccat    4440 catggctgat gcaatgcggc ggctgcatac gcttgatccg gctacctgcc cattcgacca   4500
ccaagcgaaa catcgcatcg agcgagcacg tactcggatg aagccggtc  ttgtcgatca   4560 ggatgatctg gacgaagagc atcagggggct cgcgccagcc gaactgttcg ccaggctcaa   4620
ggcgcgcatg cccgacggcg aggatctcgt cgtgacccat ggcgatgcct gcttgccgaa   4680
tatcatggtg gaaaatggcc gcttttctgg attcatcgac tgtggccggc tgggtgtggc   4740
ggaccgctat caggacatag cgttggctac ccgtgatatt gctgaagagc ttggcggcga   4800
atgggctgac cgcttcctcg tgctttacgg tatcgccgct cccgattcgc agcgcatcgc   4860
cttctatcgc cttcttgacg agttcttctg agcgggactc tggggttcga atgaccgac    4920 caagcgacgc ccaacctgcc atcacgatgg ccgcaataaa atatctttat tttcattaca   4980
tctgtgtgtt ggttttttgt gtgaatcgat agcgataagg atccgcgtat ggtgcactct   5040
cagtacaatc tgctctgatg ccgcatagtt aagccagccc cgacaccgc  caacacccgc   5100 tgacgcgccc tgacgggctt gtctgctccc ggcatccgct tacagacaag ctgtgaccgt   5160
```

```
ctccgggagc tgcatgtgtc agaggttttc accgtcatca ccgaaacgcg cgagacgaaa    5220
gggcctcgtg atacgcctat ttttataggt taatgtcatg ataataatgg tttcttagac    5280
gtcaggtggc acttttcggg gaaatgtgcg cggaacccct atttgtttat ttttctaaat    5340
acattcaaat atgtatccgc tcatgagaca ataaccctga taaatgcttc aataatattg    5400
aaaaaggaag agtatgagta ttcaacattt ccgtgtcgcc cttattccct ttttttgcggc   5460 attttgcctt cctgtttttg ctcacccaga acgctggtg aaagtaaaag atgctgaaga    5520
tcagttgggt gcacgagtgg gttacatcga actggatctc aacagcggta agatccttga    5580
gagttttcgc cccgaagaac gttttccaat gatgagcact tttaaagttc tgctatgtgg    5640
cgcggtatta tcccgtattg acgccgggca agagcaactc ggtcgccgca tacactattc    5700
tcagaatgac ttggttgagt actcaccagt cacagaaaag catcttacgg atggcatgac    5760
agtaagagaa ttatgcagtg ctgccataac catgagtgat aacactgcgg ccaacttact    5820
tctgacaacg atcggaggac cgaaggagct aaccgctttt ttgcacaaca tgggggatca    5880
tgtaactcgc cttgatcgtt gggaaccgga gctgaatgaa gccataccaa acgacgagcg    5940
tgacaccacg atgcctgtag caatggcaac aacgttgcgc aaactattaa ctggcgaact    6000
acttactcta gcttcccggc aacaattaat agactggatg gaggcggata agttgcagg    6060 accacttctg cgctcggccc ttccggctgg ctggtttatt gctgataaat ctggagccgg    6120
tgagcgtggg tctcgcggta tcattgcagc actggggcca gatggtaagc cctcccgtat    6180
cgtagttatc tacacgacgg ggagtcaggc aactatggat gaacgaaata gacagatcgc    6240
tgagataggt gcctcactga ttaagcattg gtaactgtca gaccaagttt actcatatat    6300
actttagatt gatttaaaac ttcatttta atttaaaagg atctaggtga agatcctttt    6360
tgataatctc atgaccaaaa tcccttaacg tgagttttcg ttccactgag cgtcagaccc    6420
cgtagaaaag atcaaaggat cttcttgaga tccttttttt ctgcgcgtaa tctgctgctt    6480
gcaaacaaaa aaaccaccgc taccagcggt ggtttgtttg ccggatcaag agctaccaac    6540 tcttttccg aagtaactg gcttcagcag agcgcagata ccaaatactg tccttctagt    6600
gtagccgtag ttaggccacc acttcaagaa ctctgtagca ccgcctacat acctcgctct    6660
gctaatcctg ttaccagtgg ctgctgccag tggcgataag tcgtgtctta ccgggttgga    6720
ctcaagacga tagttaccgg ataagcgca gcggtcgggc tgaacggggg gttcgtgcac    6780
acagcccagc ttggagcgaa cgacctacac cgaactgaga tacctacagc gtgagctatg    6840
agaaagcgcc acgcttcccg aagggagaaa ggcggacagg tatccggtaa gcggcagggt    6900
cggaacagga gagcgcacga gggagcttcc agggggaaac gcctggtatc tttatagtcc    6960
tgtcgggttt cgccacctct gacttgagcg tcgatttttg tgatgctcgt caggggggcg    7020
gagcctatgg aaaaacgcca gcaacgcggc cttttacgg ttcctggcct tttgctggcc    7080
ttttgctcac atggctcgac agatccattt aaattttcac cgtcatcacc gaaacgcgcg    7140
aggcagctgt ggaatgtgtg tcagttaggg tgtggaaagt ccccaggctc cccagcaggc    7200
agaagtatgc aaagcatgca tctcaattag tcagcaacca ggtgtggaaa gtccccaggc    7260
tccccagcag gcagaagtat gcaaagcatg catctcaatt agtcagcaac catagtcccg    7320
cccctaactc cgcccatccc gcccctaact ccgcccagtt ccgcccattc tccgccccat    7380
ggctgactaa ttttttttat ttatgcagag gccgaggccg cctcggccct ctgagctatt    7440
ccagaagtag tgaggaggct ttttggagg cctaggcttt tgcaaaaagc taattcgagc    7500
```

```
tcggtacccc caaacttgac ggcaatccta gcgtgaaggc tggtaggatt ttatccccgc      7560
tgccatcatg gttcgaccat tgaactgcat cgtcgccgtg tcccaaaata tggggattgg      7620
caagaacgga gaccgaccct ggcctccgct caggaacgag ttcaagtact ccaaagaat       7680 gaccacaacc tcttcagtgg aaggtaaaca gaatctggtg attatgggta ggaaaacctg      7740
gttctccatt cctgagaaga atcgaccttt aaaggacaga attaatatag ttctcagtag      7800
agaactcaaa gaaccaccac gaggagctca ttttcttgcc aaaagtttgg atgatgcctt      7860
aagacttatt gaacaaccgg aattggcaag taaagtagac atggtttgga tagtcggagg      7920
cagttctgtt taccaggaag ccatgaatca accaggccac ctcagactct tgtgacaag       7980 gatcatgcag gaatttgaaa gtgacacgtt tttcccagaa attgatttgg ggaaatataa      8040
acttctccca gaatacccag gcgtcctctc tgaggtccag gaggaaaaag gcatcaagta      8100
taagtttgaa gtctacgaga agaaagacta acaggaagat gctttcaagt tctctgctcc      8160
cctcctaaag ctatgcattt ttataagacc atgggggatg ctcgatcccc tcgcgagttg      8220
gttcagctgc tgcctgaggc tggacgacct cgcggagttc taccggcagt gcaaatccgt      8280
cggcatccag gaaaccagca gcggctatcc gcgcatccat gccccgaac tgcaggagtg       8340 gggaggcacg atggccgctt tggtccggat ctttgtgaag gaaccttact tctgtggtgt      8400
gacataattg gacaaactac ctacagagat ttaaagctct aaggtaaata taaaattttt      8460
aagtgtataa tgtgttaaac tactgattct aattgtttgt gtattttaga ttccaaccta     8520
tggaactgat gaatgggagc agtggtggaa tgccttttaat gaggaaaaacc tgttttgctc     8580 agaagaaatg ccatctagtg atgatgaggc tactgctgac tctcaacatt ctactcctcc      8640
aaaaaagaag agaaaggtag aagaccccaa ggactttcct tcagaattgc taagtttttt      8700
gagtcatgct gtgtttagta atagaactct tgcttgcttt gctatttaca ccacaaagga      8760
aaaagctgca ctgctataca agaaaattat ggaaaaatat tctgtaacct ttataagtag      8820
gcataacagt tataatcata acatactgtt ttttcttact ccacacaggc atagagtgtc      8880
tgctattaat aactatgctc aaaaattgtg tacctttagc ttttttaattt gtaaaggggt     8940 taataaggaa tatttgatgt atagtgcctt gactagagat cataatcagc ataccacat       9000 ttgtagaggt tttacttgct ttaaaaaacc tcccacacct ccccctgaac ctgaaacata      9060
aaatgaatgc aattgttgtt gttaacttgt ttattgcagc ttataatggt tacaaataaa      9120
gcaatagcat cacaaatttc acaaataaag cattttttttc actgcattct agttgtggtt     9180
tg                                                                    9182
```

<210> SEQ ID NO 5
<211> LENGTH: 11306
<212> TYPE: DNA
<213> ORGANISM: Artificial Sequence
<220> FEATURE:
<223> OTHER INFORMATION: Synthetic Sequence

<400> SEQUENCE: 5

```
aattcggatc ttcaatattg gccattagcc atattattca ttggttatat agcataaatc        60
aatattggct attggccatt gcatacgttg tatctatatc ataatatgta catttatatt       120
ggctcatgtc caatatgacc gccatgttgg cattgattat tgactagtta ttaatagtaa       180
tcaattacgg ggtcattagt tcatagccca tatatggagt tccgcgttac ataacttacg       240
gtaaatggcc cgcctggctg accgcccaac gacccccgcc cattgacgtc aataatgacg       300
tatgttccca tagtaacgcc aatagggact ttccattgac gtcaatgggt ggagtattta       360
```

```
cggtaaactg cccacttggc agtacatcaa gtgtatcata tgccaagtac gcccccctatt    420 gacgtcaatg acggtaaatg gcccgcctgg cattatgccc agtacatgac cttatgggac    480
tttcctactt ggcagtacat ctacgtatta gtcatcgcta ttaccatggt gatgcggttt    540
tggcagtaca tcaatgggcg tggatagcgg tttgactcac ggggatttcc aagtctccac    600
cccattgacg tcaatgggag tttgttttgg caccaaaatc aacgggactt tccaaaatgt    660
cgtaacaact ccgccccatt gacgcaaatg ggcggtaggc gtgtacggtg ggaggtctat    720
ataagcagag ctcgtttagt gaaccgtcag atcgcctgga gacgccatcc acgctgtttt    780
gacctccata agacaccg ggaccgatcc agcctccgcg gccgggaacg gtgcattgga    840
acgcggattc cccgtgccaa gagtgacgta agtaccgcct atagagtcta taggcccacc    900
cccttggctt cgttagaacg cggctacaat taatacataa ccttatgtat catcacata    960 cgatttaggt gacactatag aataacatcc actttgcctt tctctccaca ggtgtccact   1020
cccaggtcca actgcacctc ggttctatcg aaaacgcgcc tctagacctg caggccacca   1080
tgtccgtgct gacccaggtg ctggccctgc tgctgctgtg gctgaccggc accagatgcg   1140
acatccagat gacccagtcc ccctcctccc tgtccgcctc cgtgggcgac agagtgacca   1200
tcacctgccg ggcctcccag ggcatccgga actacctggc ctggtatcag cagaagcctg   1260
gcaaggcccc taagctgctg atctacgccg cctccaccct gcagtccggc gtgccttccc   1320
ggttctccgg ctccggcagc ggcaccgact tcaccctgac catctcctcc ctgcagcctg   1380
aggacgtggc cacctactac tgccagcggt acaacagagc cccttacacc ttcggccagg   1440
gcaccaaggt ggagatcaag cgtacggtgg ccgctccttc cgtgttcatc ttccctccct   1500
ccgacgagca gctgaagtcc ggcaccgcca gcgtcgtctg cctgctgaac aacttctacc   1560
ctcgggaggc caaggtgcag tggaaggtgg acaacgccct gcagagcggc aactcccagg   1620
aatccgtcac cgagcaggac tccaaggaca gcacctactc cctgtccagc accctgaccc   1680
tgtccaaggc cgactacgag aagcacaagg tgtacgcctg cgaggtcacc caccagggcc   1740
tgtcctcccc cgtgaccaag tccttcaacc ggggcgagtg ctgatgaaga tctgtcgacc   1800
cgggcggccg cttcccttta gtgagggtta atgcttcgag cagacatgat aagatacatt   1860
gatgagtttg gacaaaccac aactagaatg cagtgaaaaa aatgctttat ttgtgaaatt   1920
tgtgatgcta ttgctttatt tgtaaccatt ataagctgca ataaacaagt taacaacaac   1980
aattgcattc attttatgtt tcaggttcag ggggagatgt gggaggtttt ttaaagcaag   2040
taaaacctct acaaatgtgg taaaatccga taaggatcga tccgggctgg cgtaatagcg   2100
aagaggcccg caccgatcgc ccttcccaac agttgcgcag cctgaatggc gaatggacgc   2160
gccctgtagc ggcgcattaa gcgcggcggg tgtggtggtt acgcgcagcg tgaccgctac   2220
acttgccagc gccctagcgc ccgctccttt cgctttcttc ccttcctttc tcgccacgtt   2280
cgccggcttt ccccgtcaag ctctaaatcg ggggctccct ttagggttcc gatttagagc   2340
tttacggcac ctcgaccgca aaaaacttga tttgggtgat ggttcacgat cttcaatatt   2400
ggccattagc catattattc attggttata tagcataaat caatattggc tattggccat   2460
tgcatacgtt gtatctatat cataatatgt acatttatat tggctcatgt ccaatatgac   2520
cgccatgttg gcattgatta ttgactagtt attaatagta atcaattacg ggtcattag    2580 ttcatagccc atatatggag ttccgcgtta cataacttac ggtaaatggc ccgcctggct   2640
gaccgcccaa cgacccccgc ccattgacgt caataatgac gtatgttccc atagtaacgc   2700
```

```
caatagggac tttccattga cgtcaatggg tggagtattt acggtaaact gcccacttgg    2760
cagtacatca agtgtatcat atgccaagta cgcccctat tgacgtcaat gacggtaaat    2820
ggcccgcctg gcattatgcc cagtacatga ccttatggga ctttcctact ggcagtaca    2880 tctacgtatt agtcatcgct attaccatgg tgatgcggtt ttggcagtac atcaatgggc    2940
gtggatagcg gtttgactca cggggatttc caagtctcca ccccattgac gtcaatggga    3000
gtttgttttg gcaccaaaat caacgggact ttccaaaatg tcgtaacaac tccgcccat    3060 tgacgcaaat gggcggtagg cgtgtacggt gggaggtcta taagcaga gctcgtttag    3120 tgaaccgtca gatcgcctgg agacgccatc cacgctgttt tgacctccat agaagacacc    3180
gggaccgatc cagcctccgc ggccgggaac ggtgcattgg aacgcggatt ccccgtgcca    3240
agagtgacgt aagtaccgcc tatagagtct ataggcccac cccttggct tcgttagaac    3300 gcggctacaa ttaatacata accttatgta tcatacacat acgatttagg tgacactata    3360
gaataacatc cactttgcct ttctctccac aggtgtccac tcccaggtcc aactgcacct    3420
cggttctatc gaaaacgcgt ccaccatggc ctgggtctgg accctgcctt tcctgatggc    3480
cgctgcccag tccgtgcagg ccgaggtgca gctggtcgag tctggcggcg actggtgca    3540 gcctggccgt tccctgcggc tgtcctgcgc cgcctccggc ttcaccttcg acgactacgc    3600
catgcactgg gtccgccagg cccctggcaa aggcctcgag tgggtgtccg ccatcacctg    3660
gaactccggc cacatcgact acgccgactc cgtggagggc cggttcacca tctccccgga    3720
caacgccaag aactccctgt acctgcagat gaactccctg cgggccgagg acaccgccgt    3780
gtactactgc gccaaggtgt cctacctgtc caccgcctcc tccctggact actggggcca    3840
gggcaccctg gtcaccgtgt cctccgcctc caccaagggc ccctccgtgt tcctctggc    3900 cccttcctcc aagtccacct ccggcggcac cgccgctctg gctgcctgg tcaaggacta    3960 cttccctgag cctgtgacag tgtcctggaa ctctggcgcc ctgaccagcg gcgtgcacac    4020
cttccctgcc gtgctgcagt cctccggcct gtactccctg cctccgtcg tcacagtgcc    4080 ttcctccagc ctgggcaccc agacctacat ctgcaacgtg aaccacaagc cttccaacac    4140
caaggtggac aagaaggtgg agcctaagtc ctgcgacaag acccacacct gccctccctg    4200 ccctgccct gagctgctgg gcggaccttc cgtgttcctg ttccctccta gcctaagga    4260 caccctgatg atctcccgga ccctgaggt cacctgcgtg gtggtggacg tgtcccacga    4320
ggatcctgag gtcaagttca attggtacgt ggacggcgtg gaggtgcaca acgctaagac    4380
caagcctcgg gaagagcagt acaactccac ctaccgggtg gtgtccgtgc tgaccgtgct    4440
gcaccaggac tggctgaacg gcaaagaata caagtgcaag gtctccaaca aggccctgcc    4500
tgcccccatc gagaaaacca tctccaaggc caagggccag cctcgcgagc tcaggtgta    4560 caccctgcct ccctcccggg acgagctgac caagaaccag gtgtccctga cctgtctggt    4620
caagggcttc tacccttccg atatcgccgt ggagtgggag tccaacggcc agcctgagaa    4680
caactacaag accaccccctc ctgtgctgga ctccgacggc tccttcttcc tgtactccaa    4740
gctgaccgtg gacaagtccc ggtggcagca gggcaacgtg ttctcctgct ccgtgatgca    4800
cgaggccctg cacaaccact acacccagaa gtccctgtcc ctgagccctg caagtgatg    4860 aggcgcgccc ctagagtcga cccgggcggc cgcttcccct tagtgagggt taatgcttcg    4920
agcagacatg ataagataca ttgatgagtt tggacaaacc acaactagaa tgcagtgaaa    4980
aaaatgcttt atttgtgaaa tttgtgatgc tattgcttta tttgtaacca ttataagctg    5040
caataaacaa gttaacaaca caattgcat tcattttatg tttcaggttc agggggagat    5100
```

```
gtgggaggtt ttttaaagca agtaaaacct ctacaaatgt ggtaaaatcc gataaggatc    5160
gatccgggct ggcgtaatag cgaagaggcc cgcaccgatc gcccttccca acagttgcgc    5220
agcctgaatg gcgaatggac gcgccctgta gcggcgcatt aagcgcggcg ggtgtggtgg    5280
ttacgcgcag cgtgaccgct acacttgcca gcgccctagc gcccgctcct ttcgctttct    5340
tcccttcctt tctcgccacg ttcgccggct ttccccgtca gctctaaat cggggctcc     5400 ctttagggtt ccgatttaga gctttacggc acctcgaccg caaaaaactt gatttgggtg    5460
atggttcacg tagtgggcca tcgccctgat agacggtttt tcgccctttg acgttggagt    5520
ccacgttctt taatagtgga ctcttgttcc aaactggaac aacactcaac cctatctcgg    5580
tctattcttt tgatttataa gggattttgc cgatttcggc ctattggtta aaaatgagc    5640 tgatttaaca aatatttaac gcgaatttta acaaaatatt aacgtttaca atttcgcctg    5700
atgcggtatt ttctccttac gcatctgtgc ggtatttcac accgcatacg cggatctgcg    5760
cagcaccatg gcctgaaata acctctgaaa gaggaacttg gttaggtacc ttctgaggcg    5820
gaaagaacca gctgtggaat gtgtgtcagt tagggtgtgg aaagtcccca ggctccccag    5880
caggcagaag tatgcaaagc atgcatctca attagtcagc aaccaggtgt ggaaagtccc    5940
caggctcccc agcaggcaga agtatgcaaa gcatgcatct caattagtca gcaaccatag    6000
tcccgcccct aactccgccc atcccgcccc taactccgcc cagttccgcc cattctccgc    6060
cccatggctg actaattttt tttatttatg cagaggccga ggccgcctcg gcctctgagc    6120
tattccagaa gtagtgagga ggcttttttg gaggcctagg cttttgcaaa aagcttgatt    6180
cttctgacac aacagtctcg aacttaaggc tagagccacc atgattgaac aagatggatt    6240
gcacgcaggt tctccggccg cttgggtgga gaggctattc ggctatgact gggcacaaca    6300
gacaatcggc tgctctgatg ccgccgtgtt ccggctgtca gcgcaggggc gcccggttct    6360
ttttgtcaag accgacctgt ccggtgccct gaatgaactg caggacgagg cagcgcggct    6420
atcgtggctg gccacgacgg gcgttccttg cgcagctgtg ctcgacgttg tcactgaagc    6480
gggaagggac tggctgctat tgggcgaagt gccggggcag gatctcctgt catctcacct    6540
tgctcctgcc gagaaagtat ccatcatggc tgatgcaatg cggcggctgc atacgcttga    6600
tccggctacc tgcccattcg accaccaagc gaaacatcgc atcgagcgag cacgtactcg    6660 gatgaagcc ggtcttgtcg atcaggatga tctggacgaa gagcatcagg ggctcgcgcc     6720
agccgaactg ttcgccaggc tcaaggcgcg catgcccgac ggcgaggatc tcgtcgtgac    6780
ccatggcgat gcctgcttgc cgaatatcat ggtggaaaat ggccgctttt ctggattcat    6840
cgactgtggc cggctgggtg tggcggaccg ctatcaggac atagcgttgg ctacccgtga    6900
tattgctgaa gagcttggcg gcgaatgggc tgaccgcttc ctcgtgcttt acggtatcgc    6960
cgctcccgat tcgcagcgca tcgccttcta tcgccttctt gacgagttct tctgagcggg    7020 actctgggt tcgaaatgac cgaccaagcg acgcccaacc tgccatcacg atggccgcaa    7080
taaaatatct ttattttcat tacatctgtg tgttggtttt ttgtgtgaat cgatagcgat    7140
aaggatccgc gtatggtgca ctctcagtac aatctgctct gatgccgcat agttaagcca    7200
gccccgacac ccgccaacac ccgctgacgc gccctgacgg gcttgtctgc tcccggcatc    7260
cgcttacaga caagctgtga ccgtctccgg gagctgcatg tgtcagaggt tttcaccgtc    7320
atcaccgaaa cgcgcgagac gaaagggcct cgtgatacgc ctatttttat aggttaatgt    7380
catgataata atggtttctt agacgtcagg tggcacttt cggggaaatg tgcgcggaac    7440
```

```
ccctatttgt ttattttttct aaatacattc aaatatgtat ccgctcatga acaataacc      7500
ctgataaatg cttcaataat attgaaaaag aagagtatg agtattcaac atttccgtgt       7560
cgcccttatt ccctttttg cggcatttg ccttcctgtt tttgctcacc cagaaacgct       7620
ggtgaaagta aaagatgctg aagatcagtt gggtgcacga gtgggttaca tcgaactgga     7680
tctcaacagc ggtaagatcc ttgagagttt tcgccccgaa gaacgttttc caatgatgag    7740
cacttttaaa gttctgctat gtggcgcggt attatcccgt attgacgccg gcaagagca      7800
actcggtcgc cgcatacact attctcagaa tgacttggtt gagtactcac cagtcacaga    7860
aaagcatctt acggatggca tgacagtaag agaattatgc agtgctgcca taaccatgag    7920
tgataacact gcggccaact tacttctgac aacgatcgga ggaccgaagg agctaaccgc    7980
ttttttgcac aacatggggg atcatgtaac tcgccttgat cgttgggaac cggagctgaa    8040
tgaagccata ccaaacgacg agcgtgacac cacgatgcct gtagcaatgg caacaacgtt    8100
gcgcaaacta ttaactggcg aactacttac tctagcttcc cggcaacaat taatagactg    8160
gatggaggcg gataaagttg caggaccact tctgcgctcg gcccttccgg ctggctggtt    8220
tattgctgat aaatctggag ccggtgagcg tgggtctcgc ggtatcattg cagcactggg    8280
gccagatggt aagccctccc gtatcgtagt tatctacacg acggggagtc aggcaactat    8340
ggatgaacga aatagacaga tcgctgagat aggtgcctca ctgattaagc attggtaact    8400
gtcagaccaa gtttactcat atactttta gattgattta aaacttcatt tttaatttaa     8460
aaggatctag gtgaagatcc tttttgataa tctcatgacc aaaatccctt aacgtgagtt    8520
ttcgttccac tgagcgtcag accccgtaga aaagatcaaa ggatcttctt gagatccttt    8580
ttttctgcgc gtaatctgct gcttgcaaac aaaaaaacca ccgctaccag cggtggtttg    8640
tttgccggat caagagctac caactctttt tccgaaggta actggcttca gcagagcgca    8700
gataccaaat actgtccttc tagtgtagcc gtagttaggc caccacttca agaactctgt    8760
agcaccgcct acatacctcg ctctgctaat cctgttacca gtggctgctg ccagtggcga    8820
taagtcgtgt cttaccgggt tggactcaag acgatagtta ccggataagg cgcagcggtc    8880
gggctgaacg gggggttcgt gcacacagcc cagcttggag cgaacgacct acaccgaact    8940
gagataccta cagcgtgagc tatgagaaag cgccacgctt cccgaaggga gaaaggcgga    9000
caggtatccg gtaagcggca gggtcggaac aggagagcgc acgagggagc ttccaggggg    9060
aaacgcctgg tatctttata gtcctgtcgg gtttcgccac ctctgacttg agcgtcgatt    9120
tttgtgatgc tcgtcagggg gcggagcct atggaaaaac gccagcaacg cggccttttt    9180
acggttcctg gccttttgct ggcttttgc tcacatggct cgacagatcc atttaaattt    9240
tcaccgtcat caccgaaacg cgcgaggcag ctgtggaatg tgtgtcagtt agggtgtgga    9300
aagtccccag gctccccagc aggcagaagt atgcaaagca tgcatctcaa ttagtcagca    9360
accaggtgtg gaaagtcccc aggctcccca gcaggcagaa gtatgcaaag catgcatctc    9420
aattagtcag caaccatagt cccgccccta actccgccca tcccgcccct aactccgccc    9480
agttccgccc attctccgcc ccatggctga ctaattttt tatttatgc agaggccgag    9540
gccgcctcgg ccctctgagc tattccagaa gtagtgagga ggcttttttg gaggcctagg    9600
cttttgcaaa aagctaattc gagctcggta cccccaaact tgacggcaat cctagcgtga    9660
aggctggtag gattttatcc ccgctgccat catggttcga ccattgaact gcatcgtcgc    9720
cgtgtcccaa aatatgggga ttggcaagaa cggagaccga ccctgcctc cgctcaggaa    9780
cgagttcaag tacttccaaa gaatgaccac aacctcttca gtggaaggta aacagaatct    9840
```

```
ggtgattatg ggtaggaaaa cctggttctc cattcctgag aagaatcgac ctttaaagga      9900
cagaattaat atagttctca gtagagaact caaagaacca ccacgaggag ctcattttct      9960
tgccaaaagt ttggatgatg ccttaagact tattgaacaa ccggaattgg caagtaaagt     10020
agacatggtt tggatagtcg gaggcagttc tgtttaccag gaagccatga atcaaccagg     10080
ccacctcaga ctctttgtga caaggatcat gcaggaattt gaaagtgaca cgttttccc     10140 agaaattgat ttggggaaat ataaacttct cccagaatac ccaggcgtcc tctctgaggt     10200
ccaggaggaa aaaggcatca agtataagtt tgaagtctac gagaagaaag actaacagga     10260
agatgctttc aagttctctg ctcccctcct aaagctatgc atttttataa gaccatgggg     10320
gatgctcgat cccctcgcga gttggttcag ctgctgcctg aggctggacg acctcgcgga     10380
gttctaccgg cagtgcaaat ccgtcggcat ccaggaaacc agcagcggct atccgcgcat     10440
ccatgccccc gaactgcagg agtggggagg cacgatggcc gctttggtcc ggatctttgt     10500
gaaggaacct tacttctgtg gtgtgacata attggacaaa ctacctacag agatttaaag     10560
ctctaaggta aatataaaat ttttaagtgt ataatgtgtt aaactactga ttctaattgt     10620
ttgtgtattt tagattccaa cctatggaac tgatgaatgg gagcagtggt ggaatgcctt     10680
taatgaggaa aacctgtttt gctcagaaga aatgccatct agtgatgatg aggctactgc     10740
tgactctcaa cattctactc ctccaaaaaa gaagagaaag gtagaagacc ccaaggactt     10800
tccttcagaa ttgctaagtt ttttgagtca tgctgtgttt agtaatagaa ctcttgcttg     10860
ctttgctatt tacaccacaa aggaaaaagc tgcactgcta tacaagaaaa ttatggaaaa     10920
atattctgta acctttataa gtaggcataa cagttataat cataacatac tgttttttct     10980
tactccacac aggcatagag tgtctgctat taataactat gctcaaaaat tgtgtaccttt    11040 tagcttttta atttgtaaag gggttaataa ggaatatttg atgtatagtg ccttgactag     11100
agatcataat cagccatacc acatttgtag aggttttact tgctttaaaa aacctcccac     11160 acctcccct gaacctgaaa cataaaatga atgcaattgt tgttgttaac ttgtttattg     11220
cagcttataa tggttacaaa taaagcaata gcatcacaaa tttcacaaat aaagcatttt     11280
tttcactgca ttctagttgt ggtttg                                          11306

<210> SEQ ID NO 6
<211> LENGTH: 144
<212> TYPE: DNA
<213> ORGANISM: Artificial Sequence
<220> FEATURE:
<223> OTHER INFORMATION: Synthetic Sequence

<400> SEQUENCE: 6
gtaagtaccg cctatagagt ctataggccc accccttgg cttcgttaga acgcggctac        60
aattaataca taaccttatg tatcatacac atacgattta ggtgacacta tagaataaca      120
tccactttgc ctttctctcc acag                                              144
```